United States Patent
Swanson, Sr.

(10) Patent No.: US 7,351,367 B2
(45) Date of Patent: Apr. 1, 2008

(54) ADAPTER BRACKET FOR PROSTHESES, METHOD AND APPARATUS FOR FORMING PROSTHETIC DEVICE WITH TRANSFER OF PROPER ALIGNMENT

(75) Inventor: Verner M. Swanson, Sr., Temperance, MI (US)

(73) Assignee: Bionix Prosthetic Solutions, Inc., Toledo, OH (US)

( * ) Notice: Subject to any disclaimer, the term of this patent is extended or adjusted under 35 U.S.C. 154(b) by 583 days.

(21) Appl. No.: 10/823,162

(22) Filed: Apr. 12, 2004

(65) Prior Publication Data

US 2004/0204771 A1 Oct. 14, 2004

Related U.S. Application Data

(60) Provisional application No. 60/462,283, filed on Apr. 11, 2003.

(51) Int. Cl.
*B29C 33/38* (2006.01)
(52) U.S. Cl. .................. 264/222; 29/423; 29/527.1; 264/271.1; 264/278; 623/901
(58) Field of Classification Search ............ 264/222, 264/271.1, 278; 29/423, 527.1; 623/901
See application file for complete search history.

(56) References Cited

U.S. PATENT DOCUMENTS

| | | | | |
|---|---|---|---|---|
| 4,988,360 A | * | 1/1991 | Shamp | 623/33 |
| 5,246,464 A | * | 9/1993 | Sabolich | 623/33 |
| 5,658,353 A | * | 8/1997 | Layton | 623/34 |
| 5,824,111 A | * | 10/1998 | Schall et al. | 623/33 |
| 5,926,882 A | * | 7/1999 | Veith et al. | 5/658 |
| 5,972,036 A | * | 10/1999 | Kristinsson et al. | 623/33 |
| 6,077,300 A | * | 6/2000 | Sabolich et al. | 623/37 |
| 6,358,453 B1 | * | 3/2002 | Slemker et al. | 264/222 |
| 6,821,470 B2 | * | 11/2004 | Gundlapalli et al. | 264/275 |
| 6,905,519 B2 | * | 6/2005 | Swanson, Sr. | 623/36 |

* cited by examiner

*Primary Examiner*—Allan R. Kuhns
(74) *Attorney, Agent, or Firm*—Marshall & Melhorn, LLC

(57) ABSTRACT

A method of forming a prosthetic residual limb test socket utilizes an adapter bracket having generally smooth sidewalls in which a corresponding plurality of removable posts are received. The adapter bracket is secured to a model of the residual limb of a patient, and a socket forming material is applied about at least a portion of the model and the adapter bracket. The socket forming material covers the plurality of removable posts but not the lower mounting face of the adapter bracket. The adapter bracket is removable and reusable. In a further aspect, a method is provided for forming a prosthetic residual limb socket based upon a test socket, in which a casting anchor is positioned within the test socket, the casting anchor being engaged with an alignment member extending out through a hole in the test socket. A molding material is introduced into the test socket so as to at least partially encase the casting anchor, and the molding material is allowed to set to form a model. The test socket is separated from the model and the casting anchor is disengaged from the alignment member. An adapter bracket having at least one through-hole is then placed adjacent the model and the alignment member is introduced through the at least one through-hole in the adapter bracket and into engagement with the casting anchor to position the adapter bracket relative to the model. A prosthetic residual limb socket is then formed about the model and adapter bracket, the alignment member is disengaged from the casting anchor, and the prosthetic residual limb socket is separated from the model.

19 Claims, 21 Drawing Sheets

ADAPTER BRACKET FOR PROSTHESES, METHOD AND APPARATUS FOR FORMING PROSTHETIC DEVICE WITH TRANSFER OF PROPER ALIGNMENT

RELATED APPLICATION

This application is claiming the benefit, under 35 U.S.C. § 119(e), of the provisional application filed Apr. 11, 2003 under 35 U.S.C. § 111(b), which was granted Ser. No. 60/462,283. This provisional application is hereby incorporated by reference.

BACKGROUND OF THE INVENTION

The invention relates to prosthetic devices and methods of forming the same. In particular, the invention relates to a method of forming both transfemoral and transtibial, test or temporary and final, permanent sockets, and an adapter bracket for use therewith. The invention also relates to a method for transferring the alignment of a lock mechanism and/or socket attachment adapter bracket from a test socket to a final socket.

In the known prosthetic devices, the residual limb socket is connected, typically via a lock mechanism, to a prosthetic limb. The prosthetic limb is conventionally secured to an amputee's residual limb stump by securing the prosthetic limb to a rigid socket assembly. This may be done using suction, harnesses, etc. or combinations thereof. It is commonly done through the use of a locking pin. In this technique, the amputee first dons a sock-like liner formed of an elastomer, and which may include a fabric cover. The lower or distal end of the liner is formed of a rigid material, such as urethane, and the locking pin extends from this rigid bottom. These liners are well known in the art. The locking pin is extended through the wall of the socket and a distal adapter mounted within or outside of the socket, and can be locked onto a prosthetic lock mounted to the prosthetic limb to secure the prosthesis. Typically, the lock pin can be released only by moving a pinion gear in a direction parallel to its rotational axis until it disengages from the lock pin, e.g., via a manual release button.

In the conventional fabrication process, an initial design is determined for the prosthesis, perhaps with the aid of computer-aided design and manufacturing (CAD/CAM) systems, and a plaster model of the residual limb is created. Then, a "test socket" is formed on the plaster model. The test socket is placed on the patient and, if the fit of the test socket can be improved, revisions may be made and the process repeated until the desired fit is obtained. At that point, the test socket is filled with molding plaster to create a final plaster model for use in creating the final or permanent socket. Once the molding plaster has cured, the final plaster model is separated from the test socket, typically using a cast saw to cut away the test socket. In any event, the test socket must be cut apart to remove the adapter bracket and lock mechanism, if any, for use in the final socket. A final or permanent socket is then fabricated, either laminated or of the thermoplastic resin type, using the final plaster model. Typically, a vertical alignment transfer jig is relied upon in an attempt to recreate in the final socket the orientation of the adapter bracket relative to the socket found to be desirable in the test socket.

SUMMARY OF THE INVENTION

The invention relates to a method of forming a prosthetic residual limb test socket and an adapter bracket therefore. The adapter bracket includes an upper mounting face, a lower mounting face and a generally smooth sidewall extending therebetween, the sidewall including a plurality of bores in which a corresponding plurality of removable posts are received. The adapter bracket is secured to a model of the residual limb of a patient. Then, a socket forming material is applied about at least a portion of the model and the adapter bracket. The socket forming material covers the plurality of removable posts but not the lower mounting face of the adapter bracket. The socket forming material may be applied so as not to cover the lower mounting face, or any socket forming material that is initially applied to the lower mounting face may be subsequently removed, such as by cutting. The adapter bracket is thus removable and reusable.

In another aspect of the invention, a method is provided for forming a prosthetic residual limb socket based upon a test socket. The method comprises positioning a casting anchor within the test socket, the casting anchor being engaged with an alignment member extending out through a hole in the test socket. A molding material is introduced into the test socket so as to at least partially encase the casting anchor, and the molding material is allowed to set to form a model. The test socket is separated from the model and the casting anchor is disengaged from the alignment member. An adapter bracket having at least one through-hole is placed adjacent the model and the alignment member is introduced through the at least one through-hole in the adapter bracket and into engagement with the casting anchor to position the adapter bracket relative to the model. A prosthetic residual limb socket is then formed about the model and adapter bracket, the alignment member is disengaged from the casting anchor, and the prosthetic residual limb socket is separated from the model.

BRIEF DESCRIPTION OF THE DRAWINGS

The advantages of the invention will become readily apparent to those skilled in the art from the following detailed description of the preferred embodiments when considered in the light of the accompanying drawings, in which.

DETAILED DESCRIPTION OF THE PREFERRED EMBODIMENTS

Figure 1:
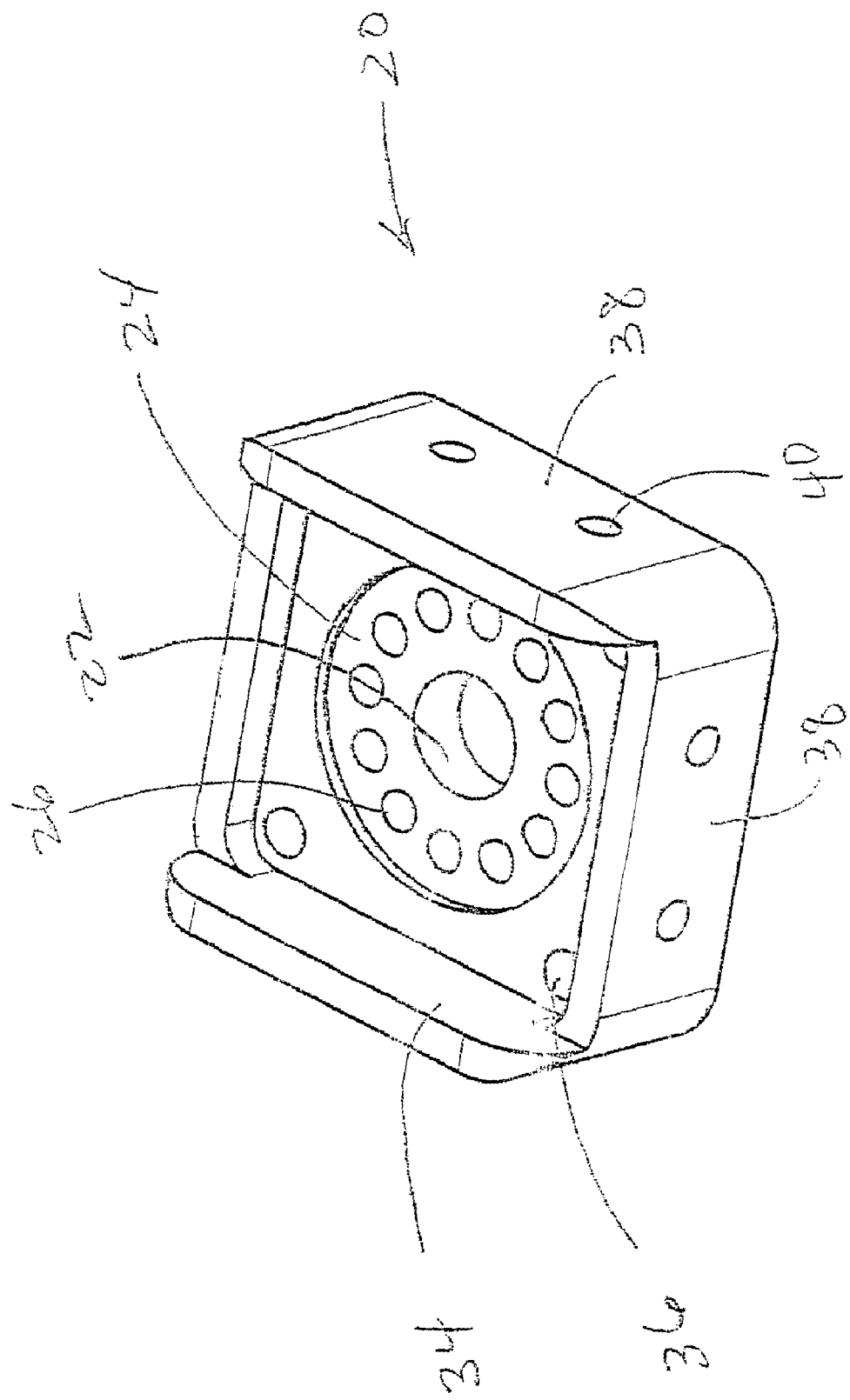
FIG. 1 is a perspective view of a first embodiment of an adapter bracket in accordance with invention that is adapted for use in a test socket and with a lock mechanism, and being removable and reusable.

The adapter brackets of the invention and methods of use thereof allow connection of a transtibial or transfemoral socket to a socket attachment plate and a suction locking mechanism during the fabrication of the test socket (thermoforming) or permanent thermoformed socket or laminated socket (thermosetting resin). The method eliminates the use of bonding and filler materials to bond and reinforce the test socket or laminated socket. The method also eliminates the application of a second or final lamination to a laminated below knee or above knee socket.

Also provided is an adapter bracket whereby the socket attachment plate and the suction lock mechanism are removable, reusable and replaceable. The method allows the alignment of the lock mechanism to be adjusted in several planes (4 or more) to increase functionality and comfort to the patient.

In certain embodiments, the adapter bracket for connecting a transtibial or transfemoral socket to a socket attachment plate is used with a quarter moon shaped, C shaped or L shaped heat formable foam during the fabrication of the test socket (thermoforming) or permanent thermoformed socket. The heat formable foam is attached to the mold with nails or other fasteners.

The adapter bracket preferably has four or more flat weight bearing areas to act as a foundation of the test socket (thermoforming) or permanent thermoformed socket or laminated socket. In certain preferred embodiments, the adapter bracket includes 12 hole round pattern to accept and fasten various shuttle and clutch lock mechanisms that have, for example, six hole patterns for the fabrication of the test socket (thermoforming) or permanent thermoformed socket or laminated socket (thermosetting resin).

In addition, a hard fabrication block may be used to lengthen the thermoplastic during vacuum forming to strengthen and add durability to the plastic and allow the socket attachment plate and suction locking mechanism to be removable, reusable and replaceable in a test socket (thermoforming) or permanent thermoformed socket.

In certain preferred embodiments, the adapter bracket may include undercuts with a vacuum hole therein to secure the adapter to the test socket (thermoforming) or permanent thermoformed socket, and to prevent the suction from pulling to hard and popping a hole in the thermoplastic during vacuum forming.

In certain preferred embodiments, the adapter bracket may include a relatively large undercut tie in ring to tie off the lamination and secure the adapter for a stronger lamination for a laminated socket (thermosetting resin).

In certain preferred embodiments, the adapter bracket may include a grooved undercut all around the adapter bracket to house an O-ring to enhance an air or suction seal, where applicable, to secure the adapter bracket for the fabrication of the test socket (thermoforming) or permanent thermoformed socket or laminated socket (thermosetting resin).

In certain preferred embodiments, the adapter bracket may include a raised round underbody that is tapped to house various mini suction valves and air expulsion mechanisms to offer the prosthetist and the amputee more options in the design of the prosthesis for the fabrication of the test socket (thermoforming) or permanent thermoformed socket or laminated socket (thermosetting resin).

In certain preferred embodiments, the adapter bracket may include a raised round and tapped underbody to house various round lock pin covers with an O-ring that thread into the adapter for a closed suction system or air expulsion mechanisms to offer the prosthetist and the amputee more options in the design of the prosthesis for the fabrication of the test socket (thermoforming) or permanent thermoformed socket or laminated socket (thermosetting resin).

In certain preferred embodiments, the adapter bracket may include a raised round and tapped underbody to house a round threaded plug with an O-ring that thread into the adapter for a closed suction system or air expulsion mechanisms to offer the prosthetist and the amputee more options in the design of the prosthesis for the fabrication of the test socket (thermoforming) or permanent thermoformed socket or laminated socket (thermosetting resin).

In certain preferred embodiments, the adapter bracket may include lengthener plates undercut to increase length on the prosthesis or to increase the length needed to house various options such as lock pin cover or a round threaded plug with an O-ring that thread into the adapter for a closed suction system or air expulsion mechanisms to offer the prosthetist and the amputee more options in the design of the prosthesis for the fabrication of the test socket (thermoforming) or permanent thermoformed socket or laminated socket (thermosetting resin).

In certain preferred embodiments, adapter brackets may be provided having various preset angles in order that the lock mechanism will have a preset amount of flexion, extension, abduction or adduction to offer the prosthetist and the amputee more alignment options in the design of the prosthesis for the fabrication of the test socket (thermoforming) or permanent thermoformed socket or laminated socket (thermosetting resin).

In certain preferred embodiments, the adapter bracket may include an integrated lock mechanism. In certain preferred embodiments, the adapter bracket may include an integrated pyramid (male or female), and/or an integrated lock mechanism and an integrated pyramid (male or female).

Turning now to FIG. 1, there is shown an adapter bracket 20. In each of the embodiments of the invention, the adapter bracket may be formed of any material that may be suitably formed and have sufficient strength and dimensional stability. Preferably, the adapter brackets are formed of a metal, especially a lightweight metal such as aluminum.

The adapter bracket 20 includes a centrally located bore 22 extending from a top surface to a bottom surface of the adapter bracket 20. The bore 22 is preferably tapped so that various suction adapters and/or cosmetic adapters (not shown) may be threadedly attached thereto. Examples of suitable suction adapters would include a plug to completely seal the central, a plug incorporating a one-way valve, and a lock pin cover.

Figure 2:
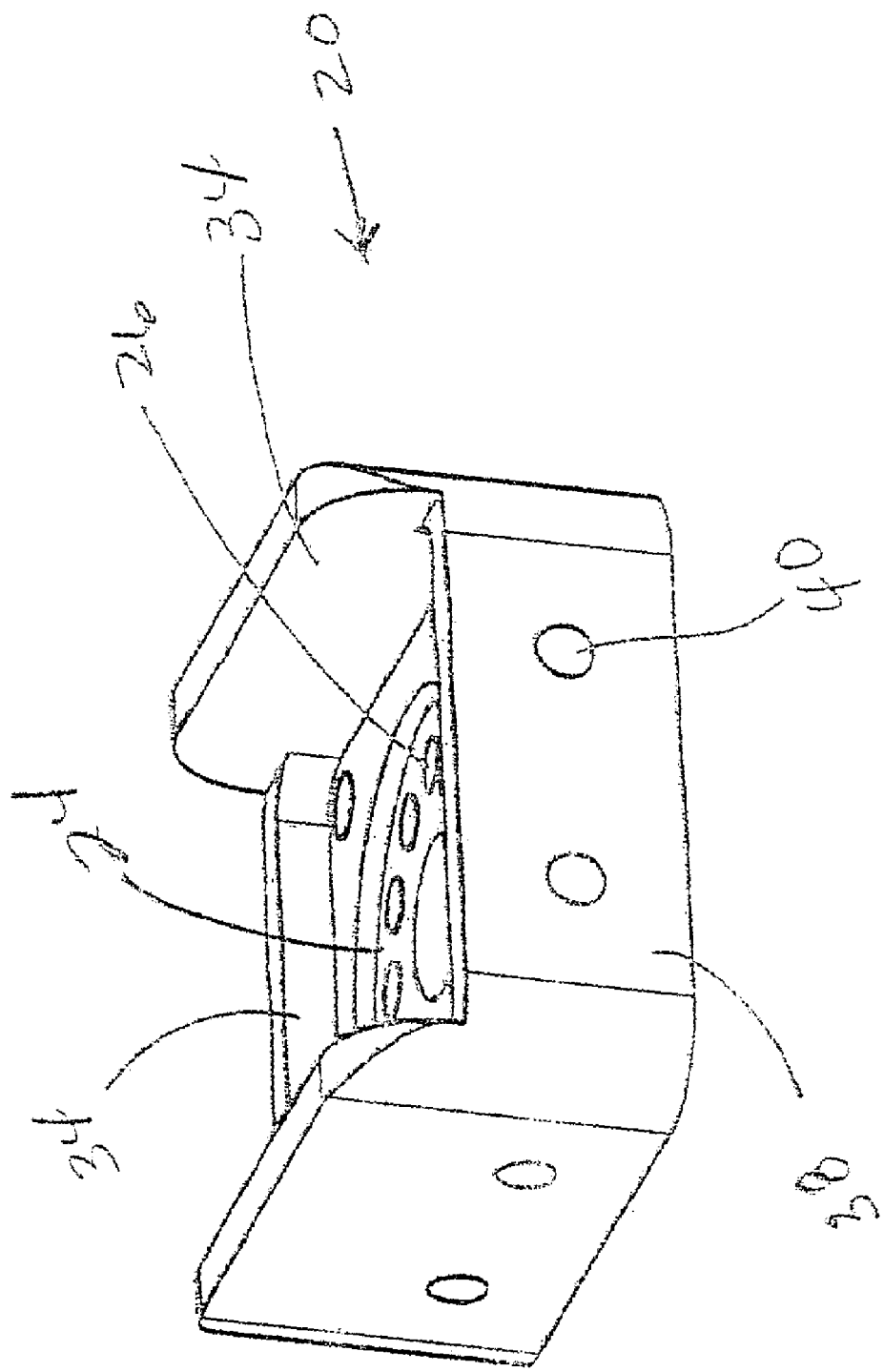
FIG. 2 is another perspective view of the adapter bracket of FIG. 1.
Figure 3:
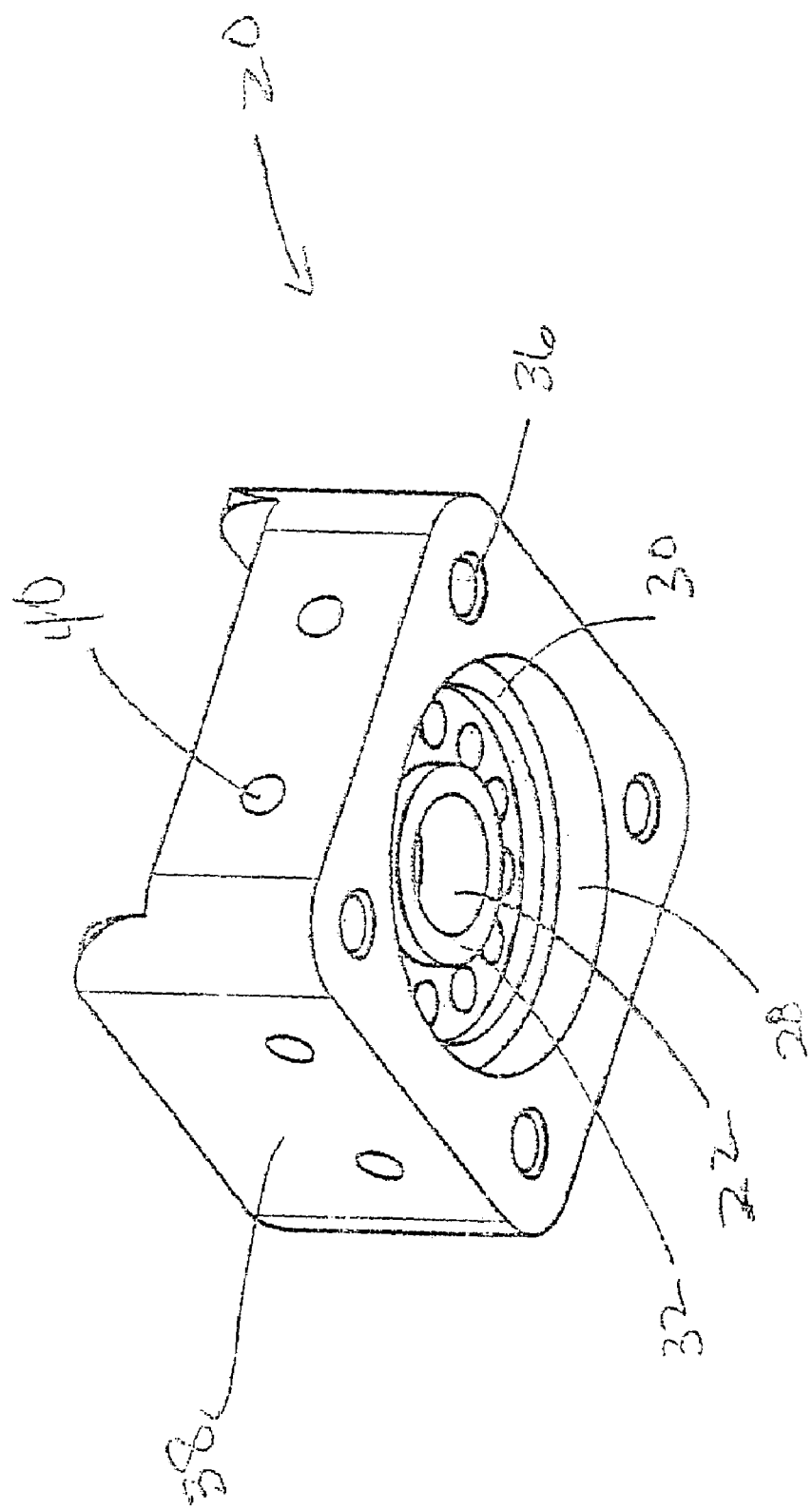
FIG. 3 is a further perspective taken from the bottom of the adapter bracket shown in FIG. 1.

As shown in FIGS. 1-3, a circular recess 24 is provided about and co-axial with the bore 22. A plurality of circumferentially spaced through-holes 26 are further provided within the recess 24 and radially outward from the bore 22. Preferably, twelve such holes 26 are equally spaced about the bore 22 to provide flexibility in attaching different locks. As shown in FIG. 3, a circular recess 28 is provide in the bottom surface of the adapter bracket 20 having a circular step 30. A cylindrical boss 32 is provided about the bore 22 on the bottom surface of the adapter bracket 20.

As illustrated, the adapter bracket 20 has a generally square shape when viewed in plan from the top. Sidewalls 34 extend upwardly from the top surface and threaded through-holes 36 are shown in each of the four corners within the sidewalls 34. The bottom surface of the adapter bracket 20 is generally flat other than the through-holes 36 and recess 28.

The sides 38 of the adapter bracket 20 are smooth to allow for eventual removal from a test socket and reuse. The sides are provided with tapped holes 40 adapted to receive threaded fasteners. As illustrated, a pair of holes 40 is shown on each side.

An example of the use of the adapter bracket 20 follows. The specific details and dimensions are for illustration only.

Plaster Model Preparation

1) Took a cast over a suspension liner.
2) Filled the cast with plaster keeping the pipe 2" from the bottom of the cast. The plaster model will have a center protrusion replicating the distal end of the suspension liner.
3) Drilled a ¼" hole straight down through the center protrusion 1¼" deep.
4) Flattened the distal end of the model by removing plaster until the diameter of the distal end of the model is equal to the outer dimension of the attachment tooling. Do not exceed the outer dimension of the tooling, because the socket would be too short. If too much plaster was removed, add back plaster to correct.
5) Checked how the tooling is centered on distal end of the model. Any voids between the model and the tooling should be filled with plaster to create a smooth transition.
6) Sealed the plaster model using an appropriate mold sealer such as cellulose crystals dissolved in acetone.
7) Tied a knot in the distal end of a non-stick nylon stockinette. Apply the non-stick nylon stockinette to the plaster model for a vacuum air wick. The knot should be centered on the distal end of the plaster model.
8) Painted the distal end of the cast around the knot in the nylon with a mold sealer such as cellulose crystals dissolved in acetone. This will glue down the nylon for trimming. Let dry and trim the nylon in a circular shape slightly smaller than the lock mechanism.
9) Fastened the attachment tooling with four long nails.

Lock Preparation

10) Removed the lock cartridge from the lock mechanism. Install and tighten the round fabrication sleeve with a standard screwdriver. Filled in the screwdriver slot on the round fabrication sleeve with (Fillauer) fitting gel or clay putty.
11) Attached the lock to the adapter bracket with the six screws.
12) Installed the center plug with through hole and O ring on the bottom of the adapter bracket 20 and tighten. Attached a ⅜" four-hole fabrication spacer block to the bottom of the adapter bracket with the four 6 mm socket head cap screws. Tightened the four screws to the spacer block.
13) Installed the eight 5 mm hex socket set screws in the sides of the adapter bracket. The set screws protruded 3/16" for 3/16" plastic or ¼" for ¼" plastic to mark the location for easy removal.
14) Filled any undercuts around the lock mechanism with fitting gel or clay.
15) Installed a circular foam lock block on the lock mechanism.
16) Fastened the with the adapter bracket 20 to the plaster model using a socket head cap screw provided with the lock mechanism. Prosthetist checks and adjusts the adapter bracket position for correct rotation prior to tightening.
17) Installed the two-inch cotton stockinette separator over the adapter bracket 20 and cut a small hole over each setscrew and pushed the stockinette around the setscrew until the setscrews protruded from the stockinette. If a copolymer or polypropylene temporary socket is being fabricated for your patient to wear outside of your facility with a removable adapter bracket, four 1/16" rectangular reinforcement plates are sprayed with an adhesive such as 3M Super Spray adhesive 77 and the plates are installed over the four sets of setscrews for socket attachment reinforcement.
18) Vacuum-formed the test socket using the blister or drape methods. For drape molding with an open non-welded seam, left the plastic on one side of the Vivak. Placed the side of the Vivak with the plastic facing up in the horizontal oven during the heat process. The oven temperature will vary 355-360 F for about 20 minutes. The side with the plastic on it will be turned toward the cast for vacuum forming and this will act as a separator. Fastener screws are used to secure the plastic seam if this procedure is used.

Trimming

19) Let the test socket cool down. Sanded off the plastic on top of the lock attachment bolt and removed the bolt with a hex key.
20) Trimmed out the ⅜" four-hole spacer block. Removed the four 6 mm socket head cap screws and removed the four-hole spacer block, providing access to the entire bottom of the adapter bracket.
21) Trimmed out and removed the test socket from the plaster model. Sanded and buffed the trim lines.
22) Sanded off the plastic on top of the eight 5 mm hex socket set screws and removed screws with a 5 mm hex key.

23) Sanded off the plastic covering the round fabrication sleeve and removed it with a standard screwdriver.

Assembly

24) Removed any fitting gel or stick wax residue from the lock body and threaded attachment holes. Followed the lock manufacturer's directions to reassemble the lock.
25) Installed and tightened the eight 5 mm socket head cap head screws and stainless steel washers to secure the attachment of the adapter bracket to the test socket. Tightened to a torque setting of 12 Nm or 9 foot pounds.
26) Install the other endoskeletal components according to manufacturer's directions.

Filling the Test Socket

27) Filled the locking pinhole with fitting gel or clay in order to prevent plaster from leaking into the lock mechanism. Taped over the posterior foam contour on the inside of the socket with masking tape in order to prevent the plaster from leaking into and around the lock mechanism.
28) Marked the location of the locking pin on the model for the fabrication of the definitive socket.

Figure 4:
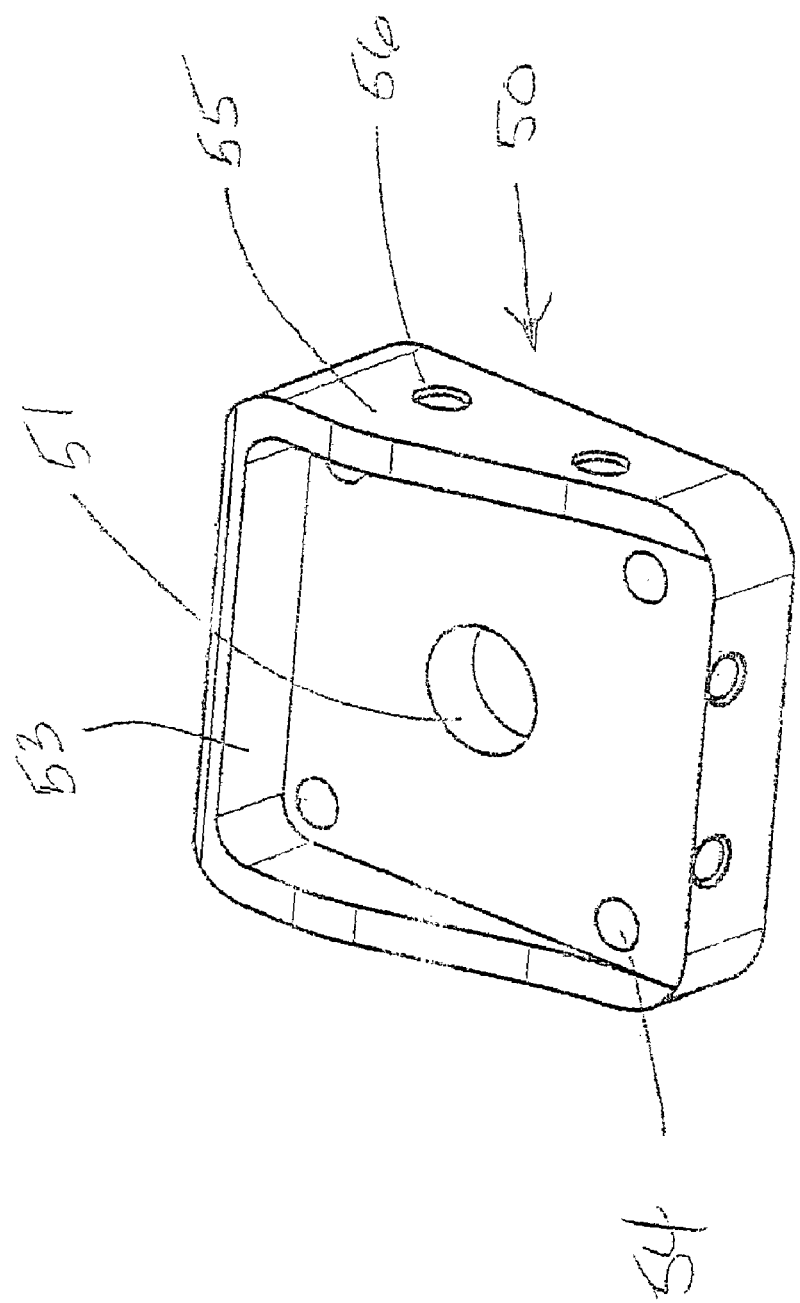
FIG. 4 is a perspective view of a second embodiment of an adapter bracket in accordance with invention that is adapted for use in a test socket and with or without a lock mechanism, and being removable and reusable.
Figure 5:
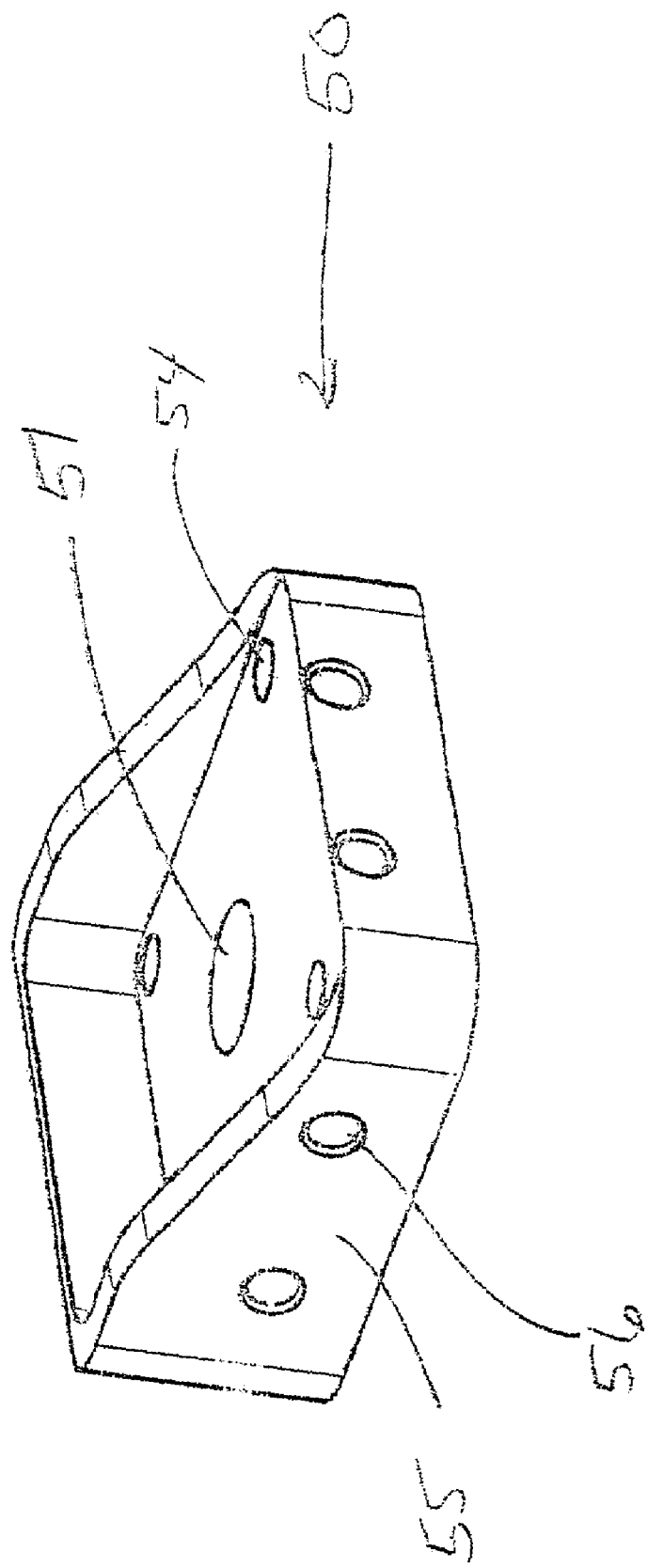
FIG. 5 is another perspective view of the adapter bracket of FIG. 4.
Figure 6:
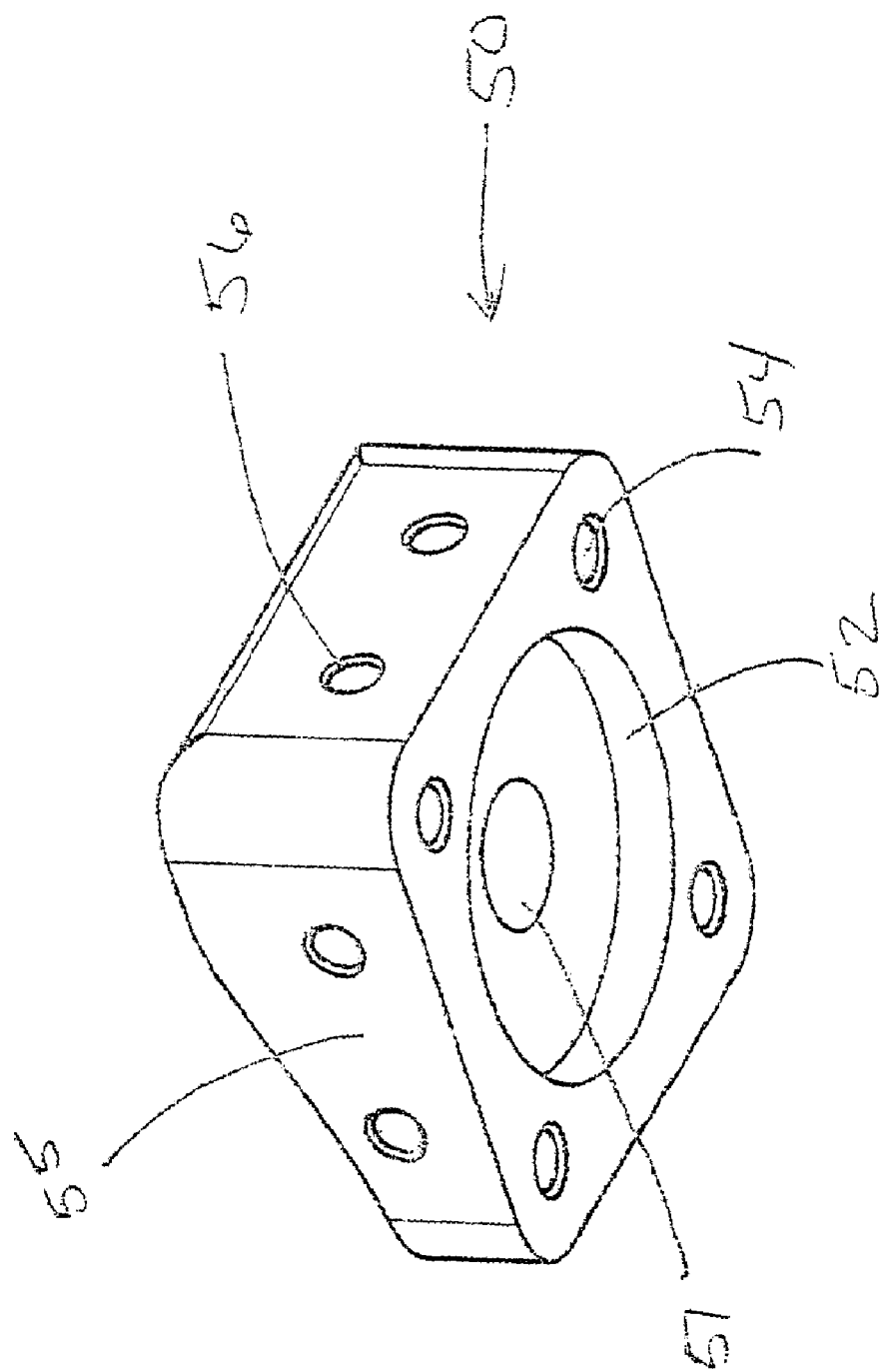
FIG. 6 is a further perspective taken from the bottom of the adapter bracket shown in FIG. 4.

Turning now to FIGS. 4-6, another embodiment of an adapter bracket is shown and denoted by the numeral 50. The adapter bracket 50 includes a centrally located bore 51 extending from a top surface to a bottom surface of the adapter bracket 50. The bore 51 is preferably tapped so that various suction adapters and/or cosmetic adapters (not shown) may be threadedly attached thereto. Examples of suitable suction adapters would include a plug to completely seal the central and a plug incorporating a one-way valve.

A circular recess 52 is provided about and co-axial with the bore 51 on the bottom surface of the adapter bracket 50, as shown in FIG. 6. As illustrated, the adapter bracket 50 has a generally square shape when viewed in plan from the top. Sidewalls 53 extend upwardly from the top surface on three of the sides, slanting downwardly to the top surface of the adapter bracket 50 on two of the opposed sidewalls 53. Threaded through-holes 54 are shown in each of the four corners within the sidewalls 53. The top and bottom surfaces of the adapter bracket 50 are generally flat other than the through-holes 54 and recess 52.

The sides 55 of the adapter bracket 50 are smooth to allow for eventual removal from a test socket and reuse. The sides are provided with tapped holes 56 adapted to receive threaded fasteners. As illustrated, a pair of holes 56 is shown on each side.

An example of the use of the adapter bracket 50 follows. The specific details and dimensions are for illustration only.

Plaster Model Preparation

1) Took the cast over the cushioned liner.
2) Filled the cast with plaster keeping the pipe 2" from the bottom of the cast.
3) Sealed the plaster model using an appropriate mold sealer such as cellulose crystals dissolved in acetone.
4) Tied a knot in the distal end of a non-stick nylon stockinette. Applied the non-stick nylon stockinette to the plaster model for a vacuum air wick. The knot should be centered on the distal end of the plaster model.
5) Painted the distal end of the cast around the knot in the nylon with a mold sealer such as cellulose crystals dissolved in acetone. This will glue down the nylon for trimming. Let dry and trimmed the nylon in a circular shape slightly smaller than the lock mechanism.
6) Attached a ⅜" four-hole fabrication spacer block to the adapter bracket 50 with the four 6 mm socket head cap screws. Tightened the four screws to the spacer block.
7) Installed eight 5 mm hex socket set screws in the sides of the adapter bracket. The setscrews protruded 3/16" for 3/16" plastic or ¼" for ¼" plastic to the mark the location for easy removal.
8) Fastened the adapter bracket to the plaster model using double stick tape to secure the posterior foam to the adapter bracket and align or bench align the components. The Prosthetist should check and adjust the adapter bracket position for correct alignment. Nail the foam to secure the adapter bracket to the model.
9) Installed the two-inch cotton stockinette separator over the adapter bracket and cut a small hole over each setscrew and pushed the stockinette around the setscrew until the setscrews protruded from the stockinette. If a copolymer or polypropylene temporary socket is being fabricated for your patient to wear outside of your facility with a removable adapter bracket, four 1/16" rectangular reinforcement plates are sprayed with an adhesive such as 3M Super Spray adhesive 77 and the plates are installed over the four sets of setscrews for socket attachment reinforcement.
10) Vacuum-formed the thermoplastic socket using the blister or drape methods. For drape molding with an open non-welded seam, leave the plastic on one side of the Vivak. Place the side of the Vivak with the plastic facing up in the horizontal oven during the heat process. The oven temperature will vary 355-360 F for about 20 minutes. The side with the plastic on it will be turned toward the cast for vacuum forming and this will act as a separator. Fastener screws will be needed to secure the plastic seam if this procedure is used.

Trimming

11) Let the thermoplastic socket cool down. Sanded off the plastic on top of the attachment bolt and removed the bolt with a hex key.
12) Trimmed out the ⅜" four-hole spacer block Removed the four 6 mm socket head cap screws with a 6 mm hex key. Removed the four-hole spacer block.
13) Trimmed out and removed the thermoplastic socket from the plaster model. Sanded and buffed the trim lines.
14) Sanded off the plastic on top of the eight 5 mm hex socket set screws and removed screws.

Assembly

15) Installed and tightened the eight 5 mm socket head cap head screws and stainless steel washers to secure the attachment of the adapter bracket to the test socket. Tightened with a 5 mm hex key to a torque setting of 12 Nm or 9 foot pounds.
16) Installed the other endoskeletal components according to manufacturer's directions.

Filling the Thermoplastic Socket

17) Taped over the posterior foam contour on the inside of the socket with masking tape in order to prevent the plaster from leaking into and around the lock mechanism.

Figure 7:
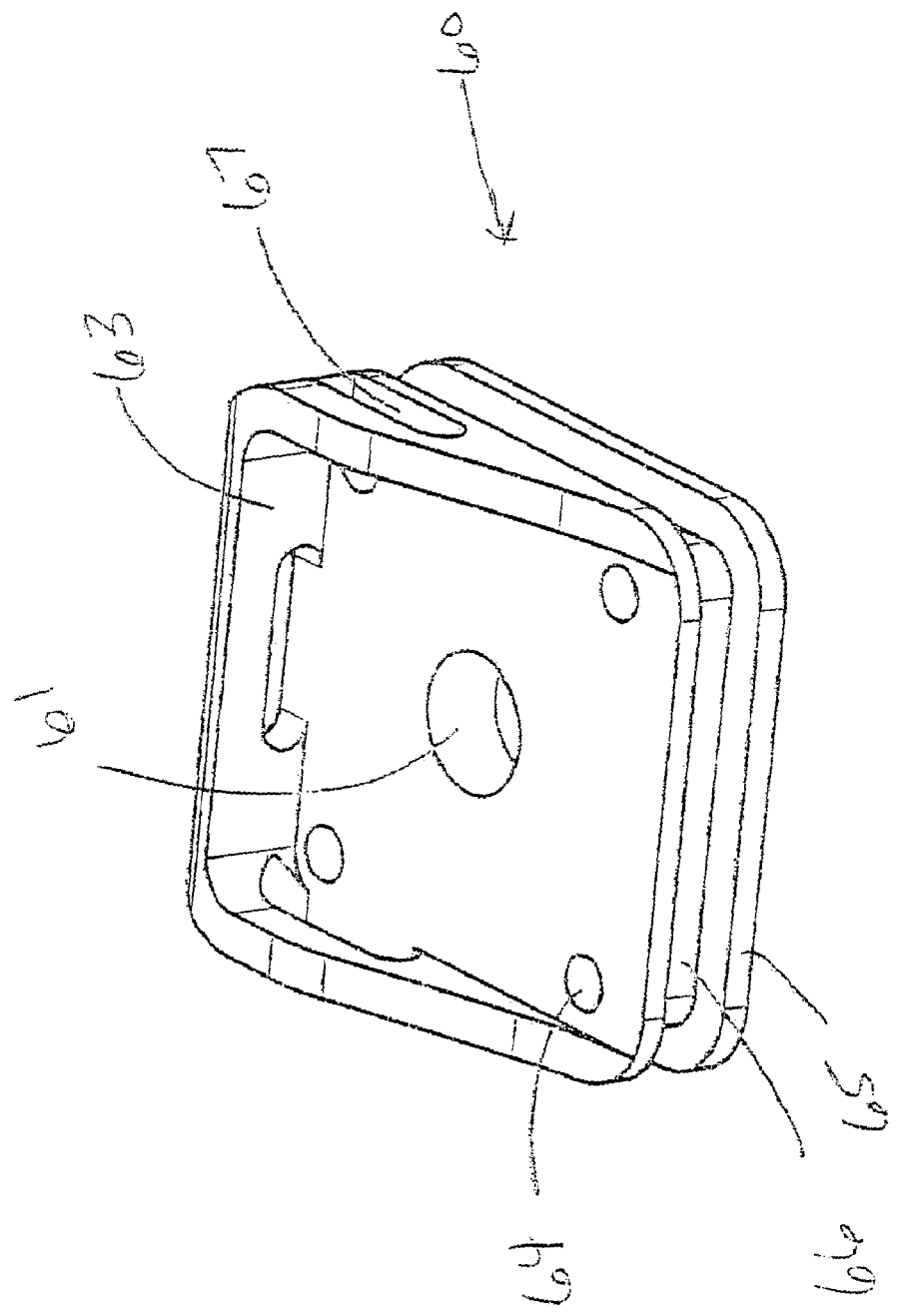
FIG. 7 is a perspective view of a third embodiment of an adapter bracket in accordance with invention that is adapted for use in a laminated final socket, with or without a lock mechanism.
Figure 8:
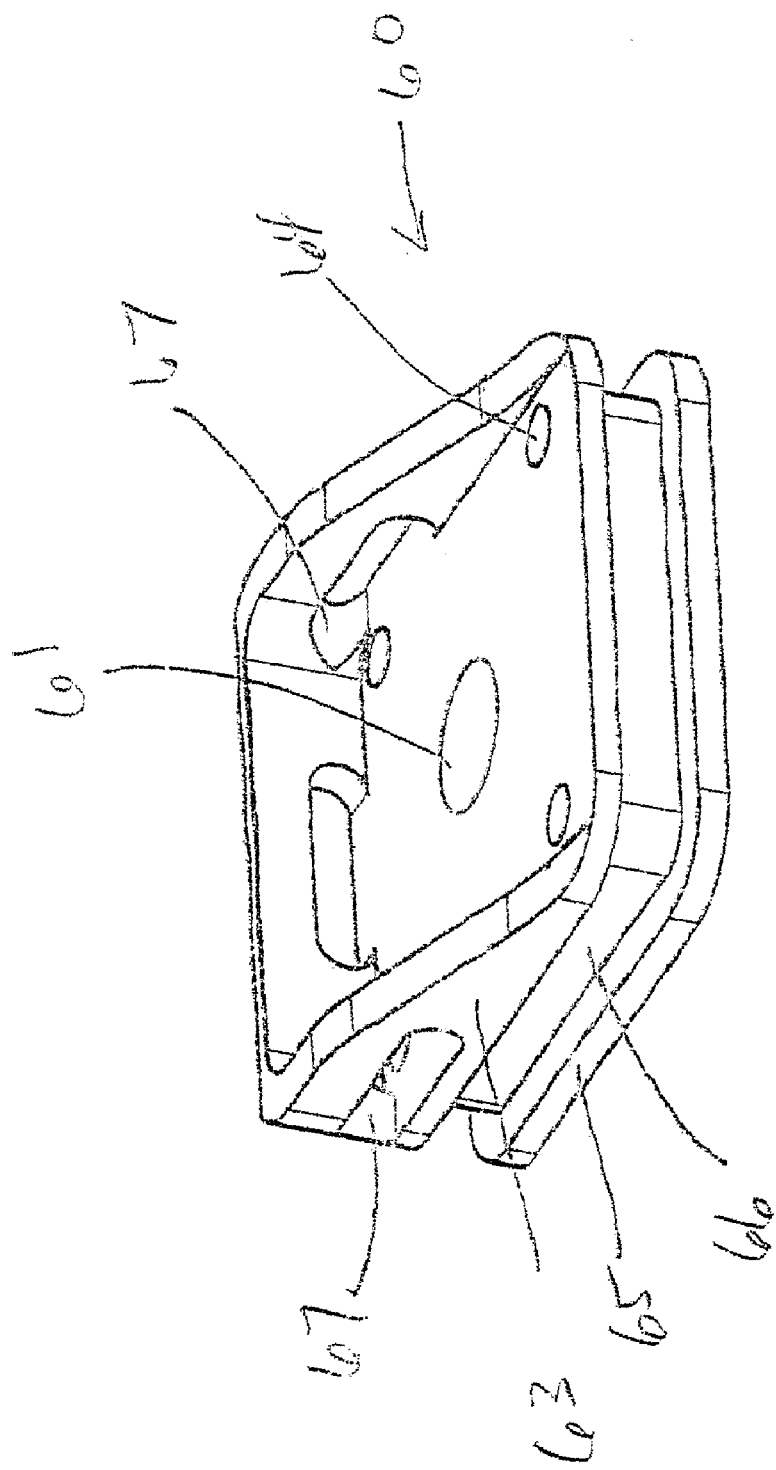
FIG. 8 is another perspective view of the adapter bracket of FIG. 7.
Figure 9:
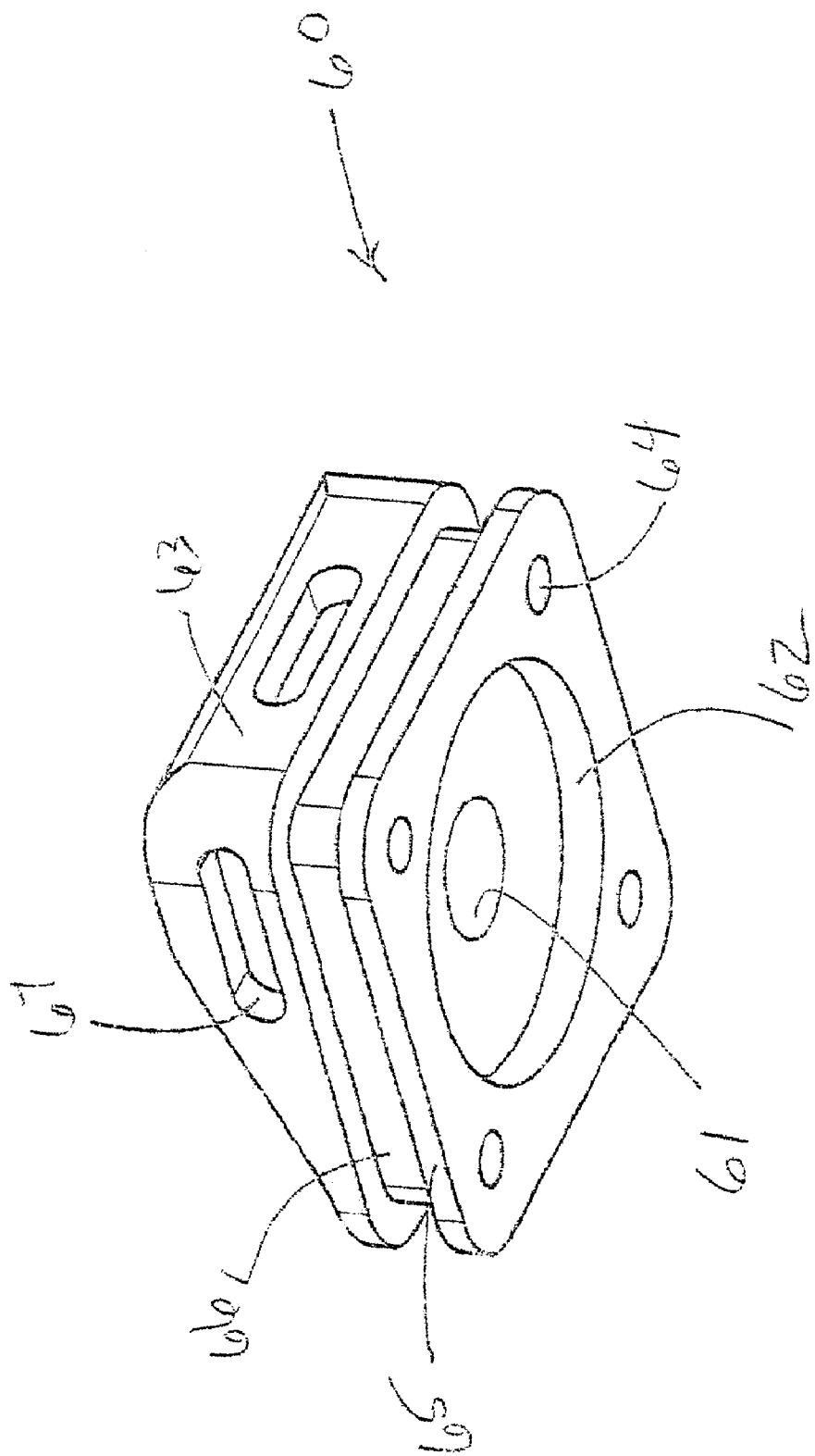
FIG. 9 is a further perspective taken from the bottom of the adapter bracket shown in FIG. 7.

Another embodiment of the adapter bracket of the invention, denoted generally by numeral 60, is illustrated in FIGS. 7-9. The adapter bracket 60 includes a centrally located bore 61 extending from a top surface to a bottom surface of the adapter bracket 60. The bore 61 is preferably tapped so that various suction adapters and/or cosmetic adapters (not shown) may be threadedly attached thereto. Examples of suitable suction adapters would include a plug to completely seal the central and a plug incorporating a one-way valve.

A circular recess 62 is provided about and co-axial with the bore 61 on the bottom surface of the adapter bracket 60, as shown in FIG. 9. As illustrated, the adapter bracket 60 has a generally square shape when viewed in plan from the top. Sidewalls 63 extend upwardly from the top surface on three of the sides, slanting downwardly to the top surface of the adapter bracket 60 on two of the opposed sidewalls 63. Threaded through-holes 64 are shown in each of the four corners within the sidewalls 63. The top and bottom surfaces of the adapter bracket 60 are generally flat other than the through-holes 64 and recess 62.

The sides 65 of the adapter bracket 60 are provided with one or more undercuts to allow the flow of material therein and increase the eventual strength of attachment. The undercut preferably takes the form of a groove 66 of rectangular cross section that extends about the entire periphery. The sidewalls 63 are also provided with slots 67 extending therethrough to allow reinforcing tape, such as carbon tape, to be fed through the slots 67.

An example of the use of the adapter bracket 60 follows. The specific details and dimensions are for illustration only.

Plaster Model Preparation

1) Took the cast over the suction liner and or cast sock.
2) Filled the cast with plaster keeping the pipe 2" from the bottom of the cast.
3) Sealed the plaster model using an appropriate mold sealer such as cellulose crystals dissolved in acetone.
4) Tied a knot in the distal end of a non-stick nylon stockinette. Applied the non-stick nylon stockinette to the plaster model for a vacuum air wick. The knot should be centered on the distal end of the plaster model.
5) Painted the distal end of the cast around the knot in the nylon with a mold sealer such as cellulose crystals dissolved in acetone. This will glue down the nylon for trimming. Let dry and trimmed the nylon in a circular shape slightly smaller than the lock mechanism.
6) Applied the PVA bag and capped the distal end.
7) Cut a round piece of stretch tape the same size as the attachment tooling and apply to the PVA over the drilled hole. The tape will help prevent the PVA from tearing. Punctured a hole in the tape over the drilled center hole. Fasten the attachment tooling with four long nails.
8) A layer of carbon tape reinforcement is applied through the slots 67 in the adapter bracket 60.
9) Considering the patient's age, weight, height, activity level and the other components used in the prosthesis, one, two or more additional layers of carbon tape reinforcement may be applied through the slots 67.
10) Lubricated the four size M6×25 mm socket head cap screws for easy removal. Attached the four-hole ⅜" square spacer block to the adapter bracket with the four socket head cap screws. Lubricated the M6×25 mm socket head cap screw and installed in a side hole in the square spacer block. Tightened all screws. Filled the screw heads with fitting gel or clay putty.

Lay-Up and Lamination

Careful consideration should be given to choice of materials used in construction of the laminated socket. The Prosthetist should consider the patient's age, weight, height, activity level and the other components used in the prosthesis. The following is an example of a standard lay-up used for an average patient.

Lay-Up Example:

11) Applied one layer of ½ ounce Dacron Felt. Punched a hole in the Dacron the same size as the attachment screw(s), being careful not to cut the PVA bag.
12) Cut a round section of ½ ounce Dacron Felt about 9" in diameter. Trimmed out a circular hole in the Dacron slightly smaller in size as the nailed round attachment tooling. Applied this round Dacron Felt on top of the first layer of felt. Placed the hole over the attachment tooling. This hides the carbon tape on the inside of the socket.
13) Applied the adapter bracket with 1" carbon tape reinforced anchor holes.
14) Fastened the adapter bracket to the plaster model using the socket head cap attachment screw. The Prosthetist should check and adjust the adapter bracket position for correct rotation, then tighten with hex key. Filled the screw head with fitting gel or clay putty.
15) Applied two layers of Nyglass stockinette. Tied the Nyglass into the tie ring and reflex back over the model. Note: Spectralon™ stockinette or the like may be substituted for Nyglass.
16) Applied two additional layers of Nyglass stockinette. Tied the Nyglass into the tie ring and reflex back over the model.
17) Applied two additional layers of Nyglass stockinette. Tie the Nyglass into the tie ring and reflex back over the model. Note: Spectralon™ stockinette may be substituted for Nyglass.
18) Applied one layer of Perlon stockinette. Note: Other finish stockinette may be substituted for Perlon.
19) Applied the outer PVA bag and pour cone. Laminated with acrylic resin such as Epox-Acryl. Tied off the excess resin with a string.

Shell Lamination for a Cosmetic Cover

21) Filled any undercuts with clay putty or fitting gel. Applied one cotton or nylon stockinette for a separator. Applied the inner PVA bag and tie off the top. Applied two nylon stockinette twisted and reflected back. Applied the PVA Bag and pour cone. Laminate with 80-20 polyester resin.

Trimming

22) Let the lamination cool down. Sanded away the material covering the end of the lamination over the attachment screw. Removed the socket head cap screw with a hex key.
23) Sanded away the material covering the end of the lamination over the five socket head cap screws. Removed the four size M6×25 mm socket head cap screws with a 5 mm hex key.
24) Trimmed out the four-hole square spacer block. Removed the four-hole square spacer block. Used the side M6×25 mm socket head cap screw to pull out the square spacer block or use channel lock pliers or the like.
25) Trimmed out and removed the socket from the plaster model. Sanded and buffed trim lines.
26) Clean off any excess plastic on the adapter bracket.

Assembly

27) Installed the other endoskeletal components according to manufacturer's directions.

Figure 10:
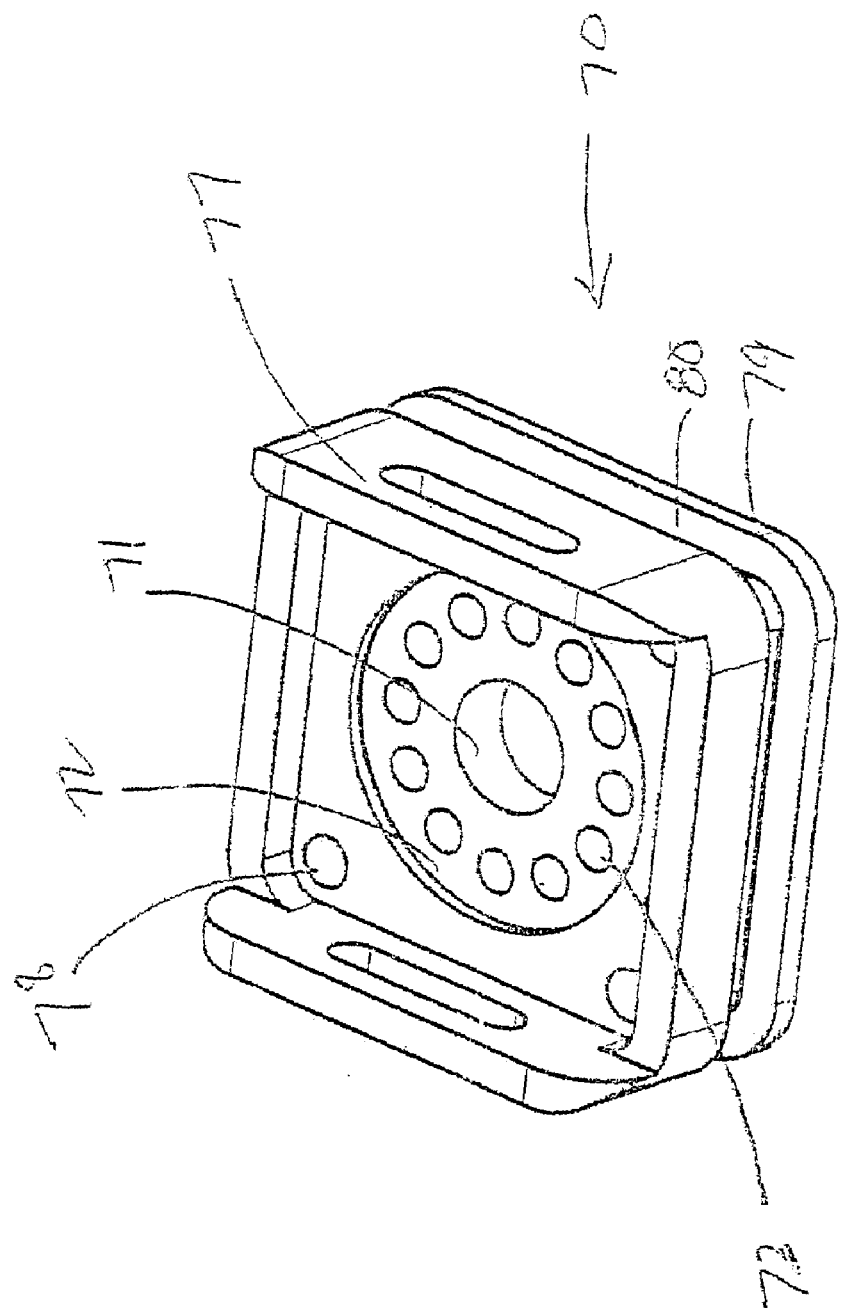
FIG. 10 is a perspective view of a fourth embodiment of an adapter bracket in accordance with invention that is adapted for use in a laminated final socket with a lock mechanism.
Figure 11:
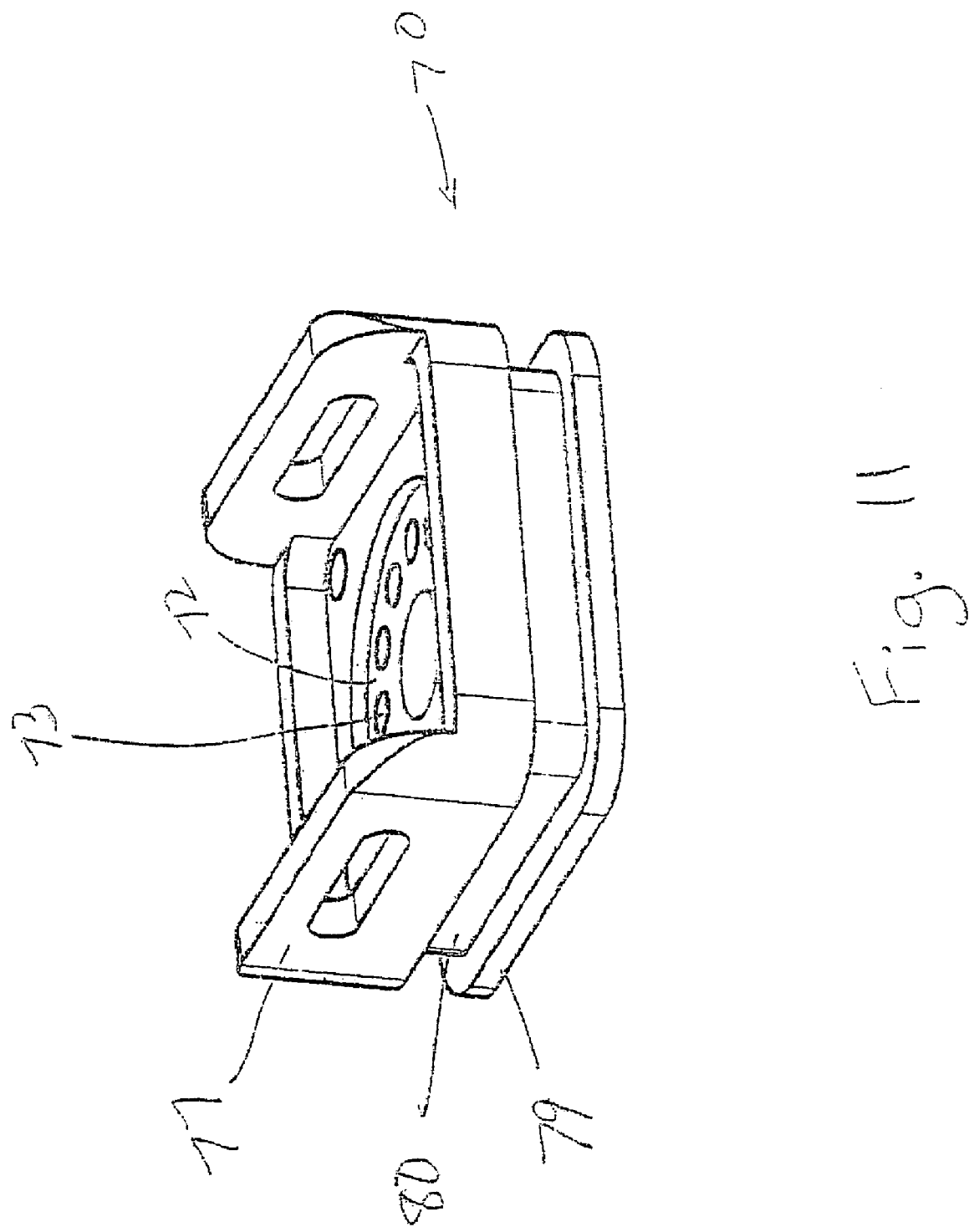
FIG. 11 is another perspective view of the adapter bracket of FIG. 10.
Figure 12:
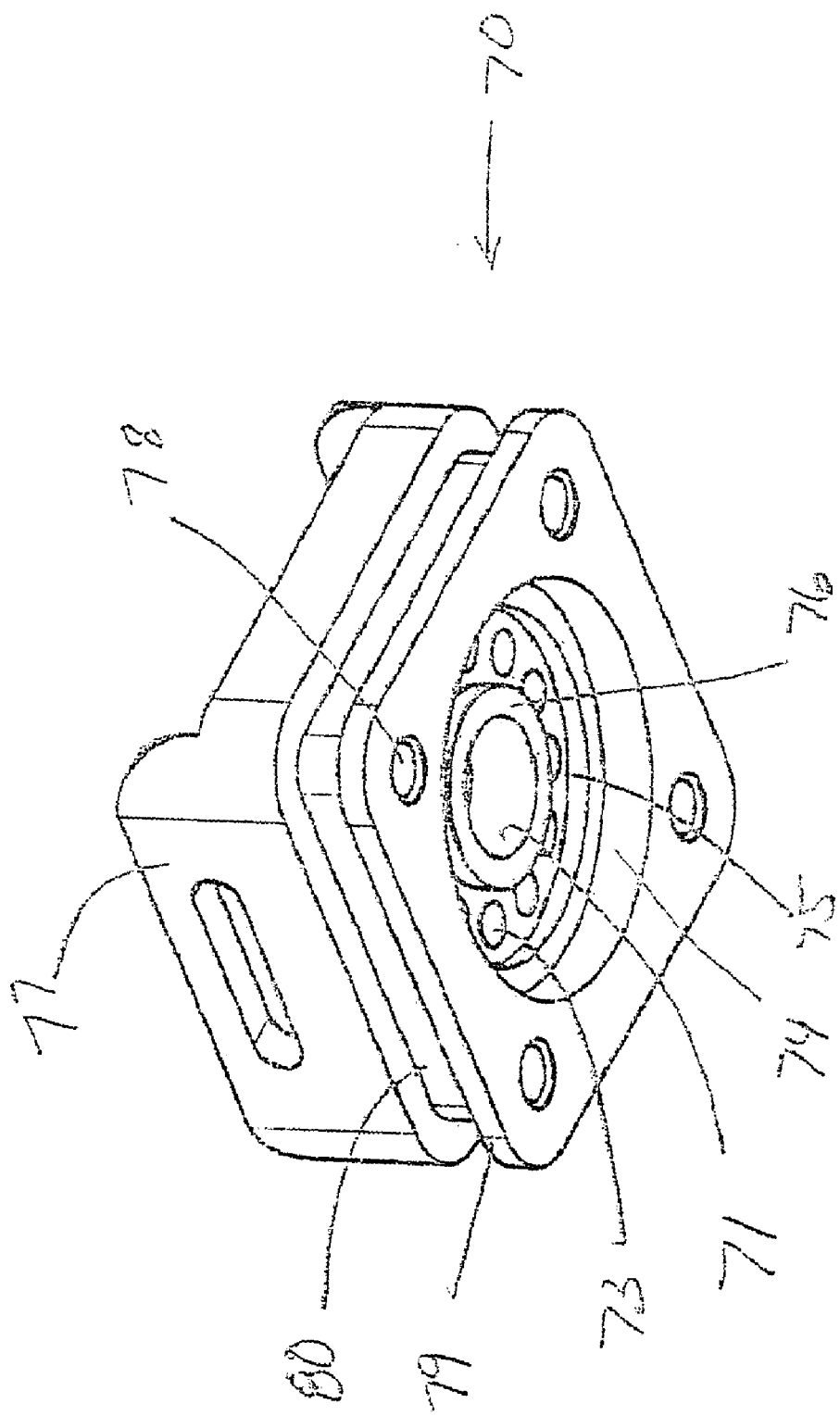
FIG. 12 is a further perspective taken from the bottom of the adapter bracket shown in FIG. 10.

Turning now to FIGS. 10-12, there is shown an adapter bracket 70. The adapter bracket 70 includes a centrally located bore 71 extending from a top surface to a bottom surface of the adapter bracket 70. The bore 71 is preferably tapped so that various suction adapters and/or cosmetic adapters (not shown) may be threadedly attached thereto. Examples of suitable suction adapters would include a plug to completely seal the central and a plug incorporating a one-way valve.

As illustrated, a circular recess 72 is provided about and co-axial with the bore 71 on the top surface. A plurality of circumferentially spaced through-holes 73 are further provided within the recess 72 and radially outward from the bore 71. Preferably, twelve such holes 73 are equally spaced about the bore 71 to provide flexibility in attaching different locks. As shown in FIG. 12, a circular recess 74 is provided in the bottom surface of the adapter bracket 70 having a circular step 75. A cylindrical boss 76 is also provided about the bore 71 on the bottom surface of the adapter bracket 70.

The adapter bracket 70 is shown having a generally square shape when viewed in plan from the top. Sidewalls 77 extend upwardly from the top surface and threaded through-holes 78 are shown in each of the four corners within the sidewalls 77. The bottom surface of the adapter bracket 70 is generally flat other than the through-holes 78 and recess 74.

The sides 79 of the adapter bracket 70 are provided with one or more undercuts to allow the flow of material therein and increase the eventual strength of attachment. The undercut preferably takes the form of a groove 80 of generally rectangular cross section that extends about the entire periphery. The sidewalls 77 are also provided with slots 81 extending therethrough to allow reinforcing tape, such as carbon tape, to be fed through the slots 81.

An example of the use of the adapter bracket 70 follows. The specific details and dimensions are for illustration only.

Plaster Model Preparation

1) Took the cast over the suspension liner.
2) Filled the cast with plaster keeping the pipe 2" from the bottom of the cast. The plaster model will have a center protrusion replicating the distal end of the suspension liner.
3) Drilled a ¼" hole straight down through the center protrusion 1¼" deep.
4) Flattened the distal end of the model by removing plaster until the diameter of the distal end of the model is equal to the outer dimension of the attachment tooling. Do not exceed the outer dimension of the tooling, because the socket would be too short. If too much plaster was removed, added back plaster to correct.
5) Checked how the tooling is centered on distal end of the model. Any voids between the model and the tooling are filled with plaster to create a smooth transition.
6) Sealed the plaster model using an appropriate mold sealer such as cellulose crystals dissolved in acetone.
7) Tied a knot in the distal end of a non-stick nylon stockinette. Applied the non-stick nylon stockinette to the plaster model for a vacuum air wick. The knot should be centered on the distal end of the plaster model.
8) Painted the distal end of the cast around the knot in the nylon with a mold sealer such as cellulose crystals dissolved in acetone. This will glue down the nylon for trimming. Let dry and trimmed the nylon in a circular shape slightly smaller than the lock mechanism.
9) Applied the PVA bag and cap the distal end.
10) Cut a round piece of stretch tape the same size as the attachment tooling and applied to the PVA over the drilled hole. The tape will help prevent the PVA from tearing. Punctured a hole in the tape over the drilled center hole. Fastened the attachment tooling with the four long nails.
11) A layer of carbon tape reinforcement is applied through the slots 81 in the adapter bracket 70.
12) Considering the patient's age, weight, height, activity level and the other components used in the prosthesis, one, two or more additional layers of carbon tape reinforcement may be applied through the slots 81.

Lock Preparation

13) Followed the lock manufacturer's directions for preparing the lock for attachment to the plaster model. Removed the lock cartridge from the lock mechanism. Filled the interior of the lock body with fitting gel or stick wax to prevent plastic from leaking into the lock. Installed and tightened the round fabrication sleeve with a standard screwdriver.
14) Attached the lock to the adapter bracket 70 with the six screws. Moved the Carbon tape to the sides to make room for the lock mechanism in the middle of the adapter. Tightened the sheet metal screws.
15) Lubricated the four size M6×25 mm socket head cap screws for easy removal. Attached the four-hole ⅜" square spacer block to the adapter bracket with the four socket head cap screws. Lubricated the M6×25 mm socket head cap screw and installed in the side hole in the square spacer block. Tightened all screws. Filled the screw heads, set screw for lock cartridge and slot in the round fabrication sleeve with fitting gel or clay putty.

Lay-Up and Lamination

Careful consideration should be given to choice of materials used in construction of the laminated socket. The Prosthetist should consider the patient's age, weight, height, activity level and the other components used in the prosthesis. The following is an example of a lay-up used for an average patient.

Lay-Up Example:

16) Applied one layer of ½ ounce Dacron Felt. Trimmed out a circular hole in the Dacron the same size as the nailed round holding spacer, being careful not to cut the PVA bag.
17) Cut a round section of ½ ounce Dacron Felt about 12" in diameter. Trimmed out a circular hole in the Dacron slightly smaller in size as the nailed round attachment tooling. Applied this round Dacron Felt on top of the first layer of felt. Placed the hole over the attachment tooling. This hides the carbon tape on the inside of the socket.
18) Applied the adapter bracket and lock with 1" carbon tape reinforced anchor slots to the plaster model.
19) Fastened the lock mechanism with the adapter bracket to the plaster model using the socket head cap screw provided with the lock mechanism. The Prosthetist should check and adjust the adapter bracket position for correct rotation, then tighten with hex key. Filled the screw head with fitting gel or clay putty.
20) Applied two layers of Nyglass stockinette. Tied the Nyglass into the tie ring and reflex back over the model. Note: Spectralon™ stockinette may be substituted for Nyglass.
21) Applied two additional layers of Nyglass stockinette. Tied the Nyglass into the tie ring and reflex back over the model.
22) Applied two additional layers of Nyglass stockinette. Tied the Nyglass into the tie ring and reflex back over the model.
23) Applied one layer of Perlon stockinette. Note: other finish stockinette may be substituted for Perlon.
24) Applied the outer PVA bag and pour cone. Laminated with acrylic resin such as Epox-Acryl.

Shell Lamination for a Cosmetic Cover

25) Filled any undercuts with clay putty or fitting gel. Applied one cotton or nylon stockinette for a separator. Applied the inner PVA bag and tie off the top. Applied two nylon stockinette twisted and reflected back. Applied the PVA Bag and pour cone. Laminated with 80-20 polyester resin.

Trimming

26) Let the lamination cool down. Sanded away the material covering the end of the lamination over the lock screw. Removed the lock socket head cap screw with a hex key.
27) Sanded away the material covering the end of the lamination over the five socket head cap screws. Removed the four size M6×25 mm socket head cap screws with a 5 mm hex key.
28) Trimmed out the four-hole square spacer block. Removed the four-hole square spacer block. Used the side M6×25 mm socket head cap screw to pull out the square spacer block or use channel lock pliers or the like.
29) Trimmed out and removed the socket from the plaster model. Sanded and buffed trim lines.
30) Sanded off the plastic covering the round fabrication sleeve and remove it with a standard screwdriver.
31) Cleaned off any excess plastic on the adapter bracket.

Assembly

32) Removed any fitting gel or stick wax residue from the lock body and threaded attachment holes. Followed the lock manufacturer's directions to reassemble the lock.
33) Installed the other endoskeletal components according to manufacturer's directions.

Figure 13:
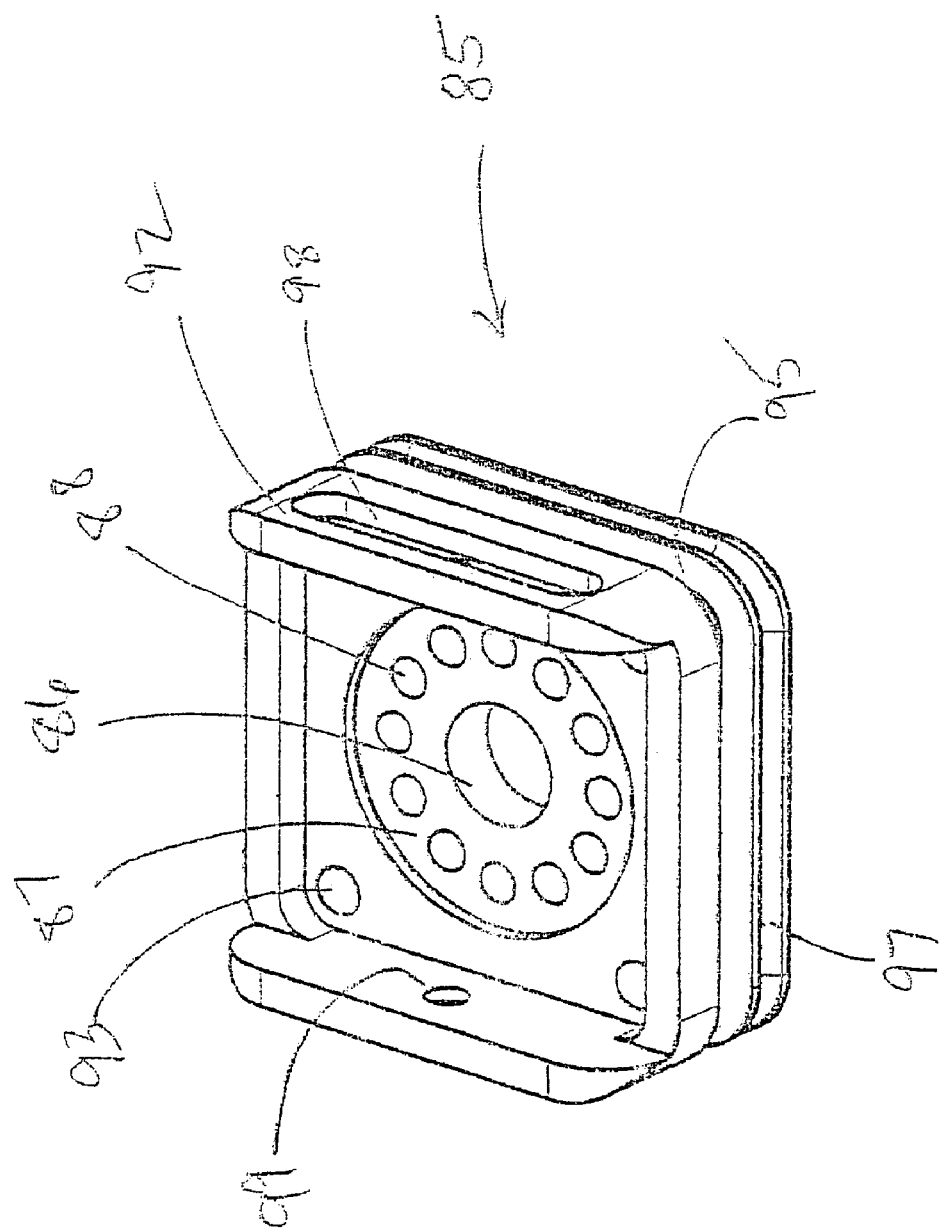
FIG. 13 is a perspective view of a fifth embodiment of an adapter bracket in accordance with invention that is adapted for use in a thermoplastic test socket with a lock mechanism.
Figure 14:
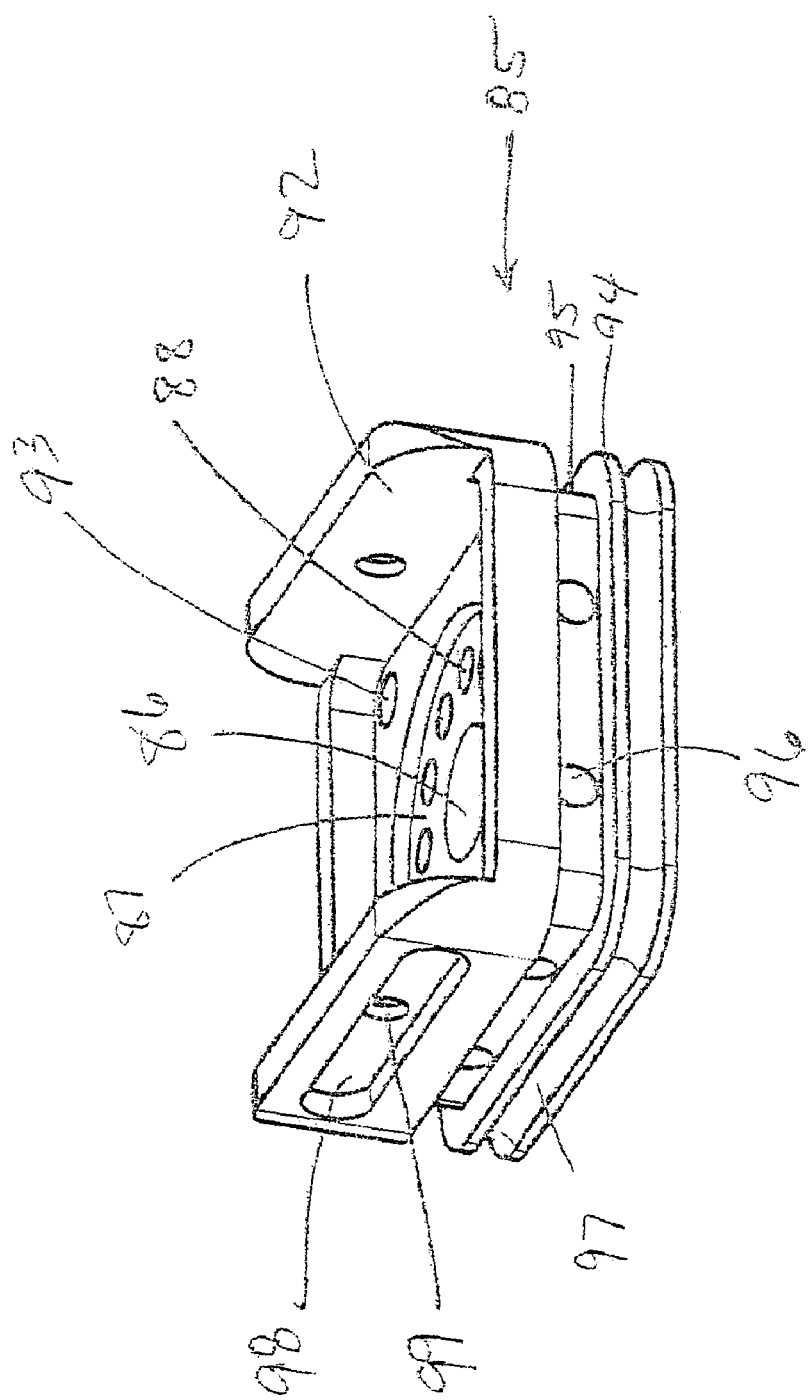
FIG. 14 is another perspective view of the adapter bracket of FIG. 13.
Figure 15:
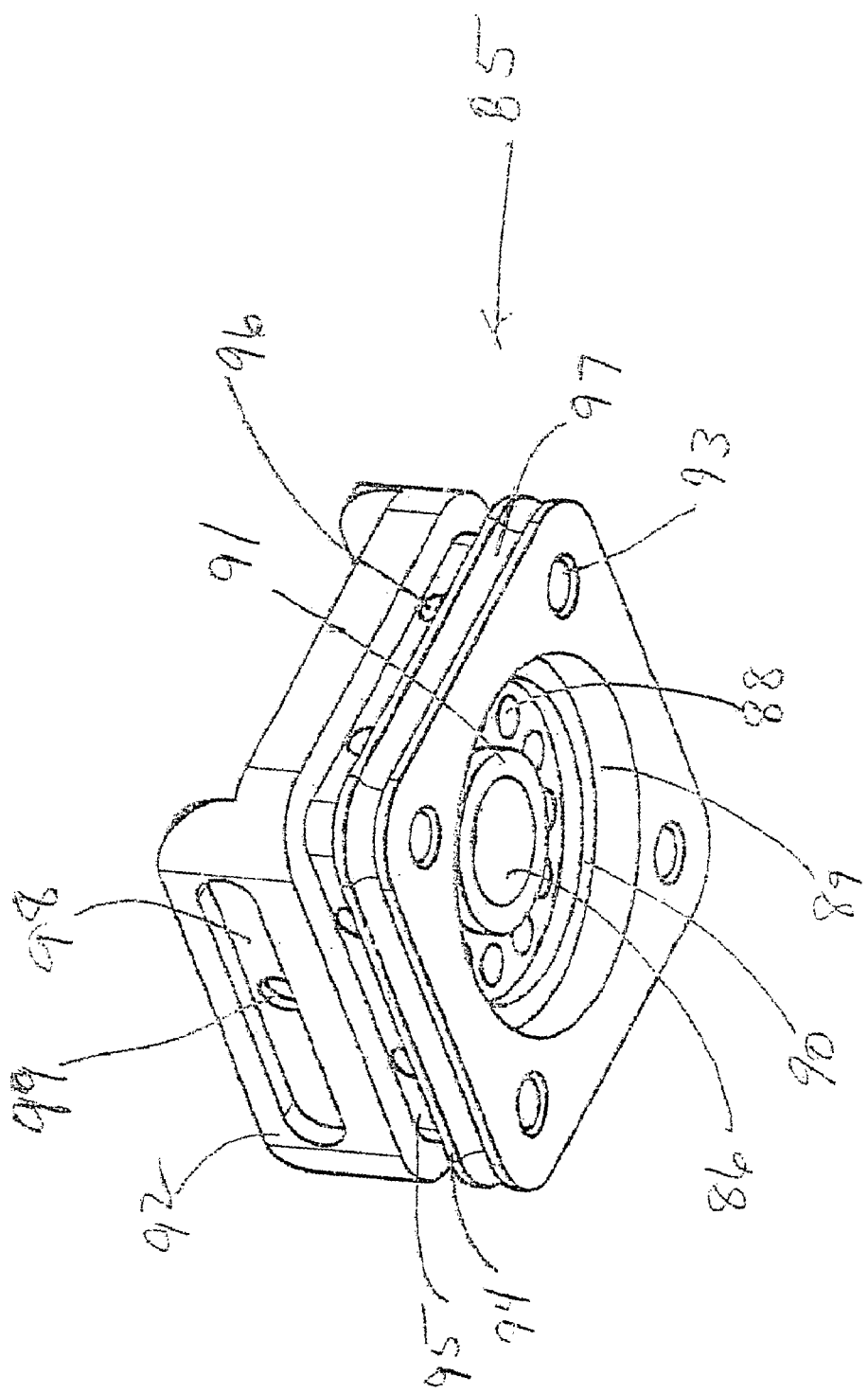
FIG. 15 is a further perspective taken from the bottom of the adapter bracket shown in FIG. 13.

The embodiment shown in FIGS. 13-15, denoted generally by numeral 85, is similar in structure to the embodiment of FIGS. 10-12. The adapter bracket 80 includes a centrally located bore 86, a circular recess 87 provided about and co-axial with the bore 86 on the top surface, and a plurality of circumferentially spaced through-holes 88 provided within the recess 87 and radially outward from the bore 86. As shown in FIG. 15, a circular recess 89 is provided in the bottom surface of the adapter bracket 85 having a circular step 90. A cylindrical boss 91 is also provided about the bore 86 on the bottom surface of the adapter bracket 85.

The adapter bracket 85 is shown having a generally square shape when viewed in plan from the top, with sidewalls 92 extending upwardly from the top surface and threaded through-holes 93 in each of the four corners. The bottom surface of the adapter bracket 85 is generally flat other than the through-holes 93 and recess 89.

The sides 94 of the adapter bracket 85 are provided with one or more undercuts, such as the groove 95 of generally rectangular cross section that extends about the entire periphery. Tapped holes 96 adapted to receive threaded fasteners are provided within the groove 95. As illustrated, a pair of holes 96 is shown on each side. The sides 94 are also provided with groove 97, preferably of generally circular cross section, that extends about the entire periphery proximate the bottom surface of the adapter bracket 85. The groove 97 is adapted to receive an O-ring. An opposed pair of the sidewalls 92 of the adapter bracket 85 are provided with undercut slots 98, each of which includes an approximately centered through-hole 99.

An example of the use of the adapter bracket 85 follows. The specific details and dimensions are for illustration only.

Plaster Model Preparation

1) Took the cast over the suspension liner.
2) Filled the cast with plaster keeping the pipe 2" from the bottom of the cast. The plaster model will have a center protrusion replicating the distal end of the suspension liner.
3) Drilled a ¼" hole straight down through the center protrusion 1¼" deep.
4) Flattened the distal end of the model by removing plaster until the diameter of the distal end of the model is equal to the outer dimension of the attachment tooling. Do not exceed the outer dimension of the tooling, because the socket would be too short. If too much plaster was removed, added back plaster to correct.
5) Checked how the tooling is centered on distal end of the model. Any voids between the model and the tooling are filled with plaster to create a smooth transition.
6) Sealed the plaster model using an appropriate mold sealer such as cellulose crystals dissolved in acetone.
7) Tied a knot in the distal end of a non-stick nylon stockinette. Applied the non-stick nylon stockinette to the plaster model for a vacuum air wick. The knot should be centered on the distal end of the plaster model.
8) Painted the distal end of the cast around the knot in the nylon with a mold sealer such as cellulose crystals dissolved in acetone. This will glue down the nylon for trimming. Let dry and trimmed the nylon in a circular shape slightly smaller than the lock mechanism.
9) Fastened the attachment tooling with the four long nails provided with the adapter bracket.

Lock Preparation

10) Read the lock manufacturer's directions for preparing the lock for attachment to the plaster model. Removed the lock cartridge from the lock mechanism. Installed and tightened the round fabrication sleeve with a standard screwdriver. Filled in the screwdriver slot on the round fabrication sleeve with (Fillauer) fitting gel or clay putty.
11) Attached the lock to the adapter bracket with the six screws. Tightened the sheet medal screws.
12) Installed the center plug with through hole and O-ring on the bottom of the adapter bracket and tightened. Attached the ⅜" four-hole fabrication spacer block to the bottom of the adapter bracket with the four 6 mm socket head cap screws. Tightened the four screws to the spacer block with a 6 mm hex key.
13) Installed the eight 5 mm hex socket set screws in the sides of the adapter bracket. The setscrews protruded 3/16" for 3/16" plastic or ¼" for ¼" plastic to the mark the location for easy removal. Tightened with a 5 mm hex key.
14) Fastened the lock mechanism with the adapter bracket to the plaster model using the socket head cap screw provided with the lock mechanism. The Prosthetist should check and adjust the adapter bracket position for correct rotation, then tighten with hex key.
15) Vacuum-formed the test socket using the blister or drape methods. For drape molding with an open non-welded seam, leave the plastic on one side of the Vivak. Place the side of the Vivak with the plastic facing up in the horizontal oven during the heat process. The oven temperature will vary 355-360 F for about 20 minutes. The side with the plastic on it will be turned toward the cast for vacuum forming and this will act as a separator. Fastener screws will be used to secure the plastic seam if this procedure is used.

Trimming

16) Let the test socket cool down. Sanded off the plastic on top of the lock attachment bolt and remove the bolt with a hex key.
17) Trimmed out the ⅜" four-hole spacer block. Removed the four 6 mm socket head cap screws with a 6 mm hex key. Removed the four-hole spacer block.
18) Trimmed out and removed the test socket from the plaster model. Sanded and buffed the trim lines.
19) Sanded off the plastic on top of the eight 5 mm hex socket set screws and removed screws with a 5 mm hex key.
20) Sanded off the plastic covering the round fabrication sleeve and removed it with a standard screwdriver.

Assembly

21) Removed any fitting gel or stick wax residue from the lock body and threaded attachment holes. Followed the lock manufacturer's directions to reassemble the lock.
22) Installed and tightened the eight 5 mm socket head cap head screws and stainless steel washers to secure the attachment of the adapter bracket to the test socket. Tightened with a 5 mm hex key to a torque setting of 12 Nm or 9 foot pounds.
23) Installed the other endoskeletal components according to manufacturer's directions.

Figure 16:
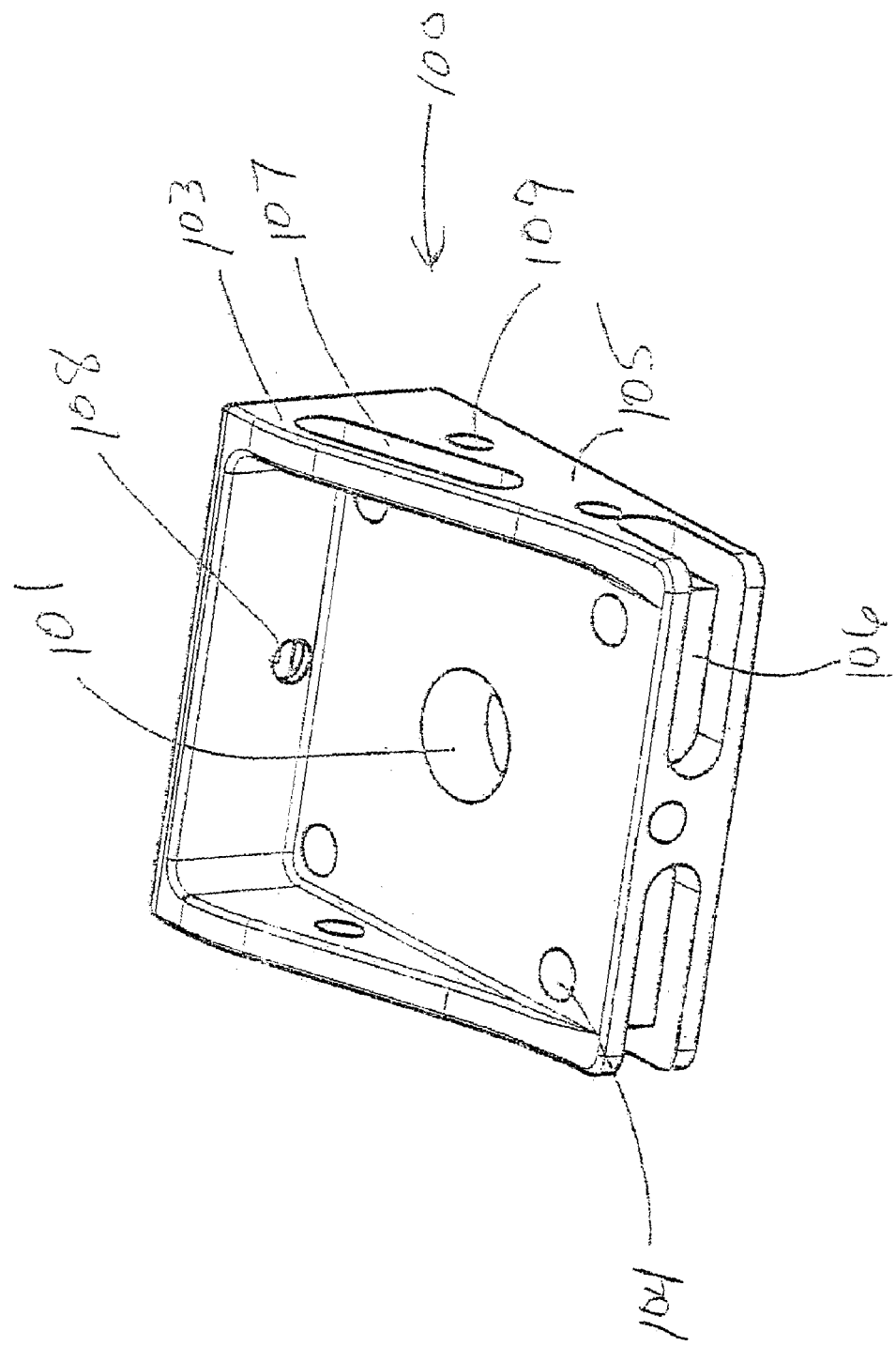
FIG. 16 is a perspective view of a sixth embodiment of an adapter bracket in accordance with invention that is adapted for use in a thermoplastic test socket, with or without a lock mechanism.
Figure 17:
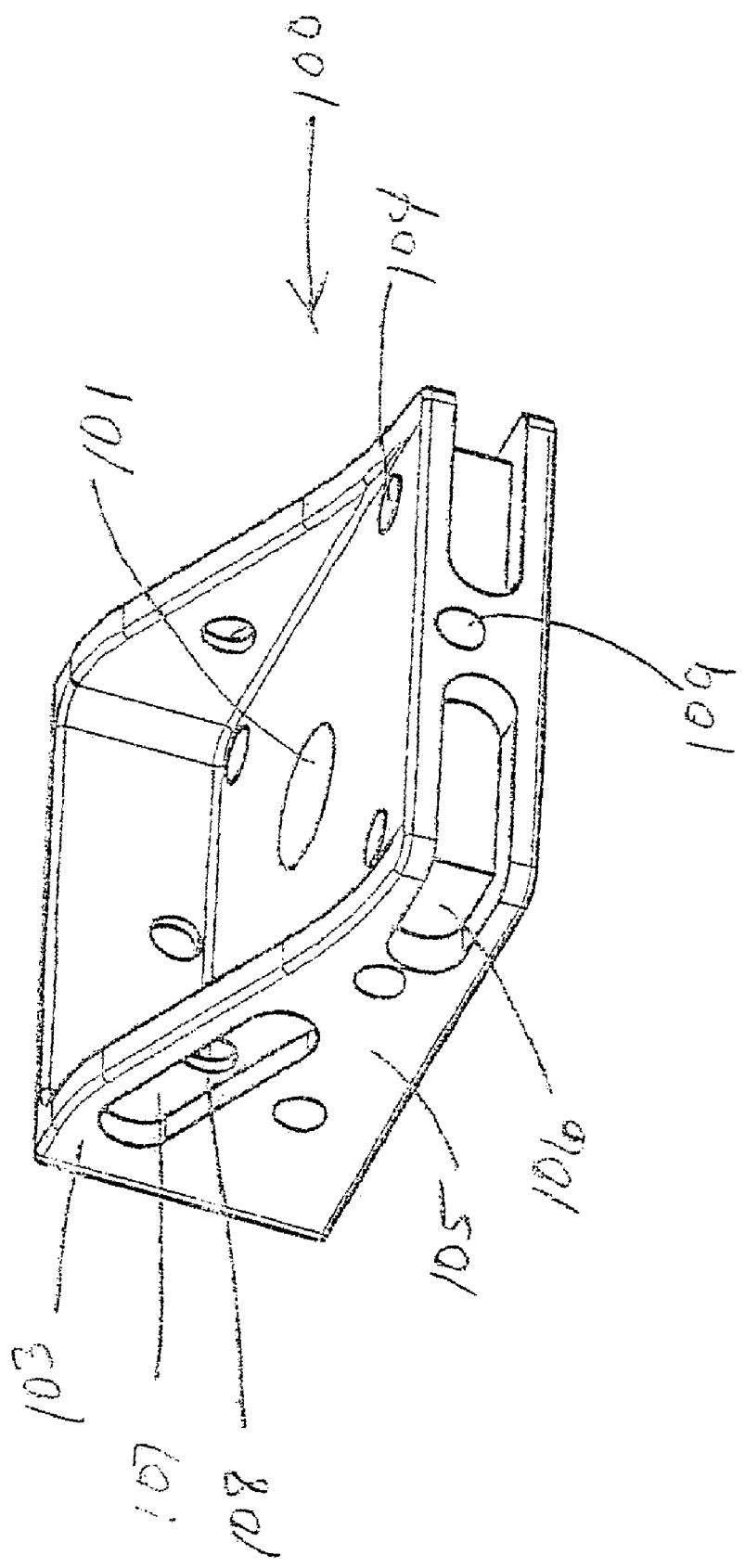
FIG. 17 is another perspective view of the adapter bracket of FIG. 16.
Figure 18:
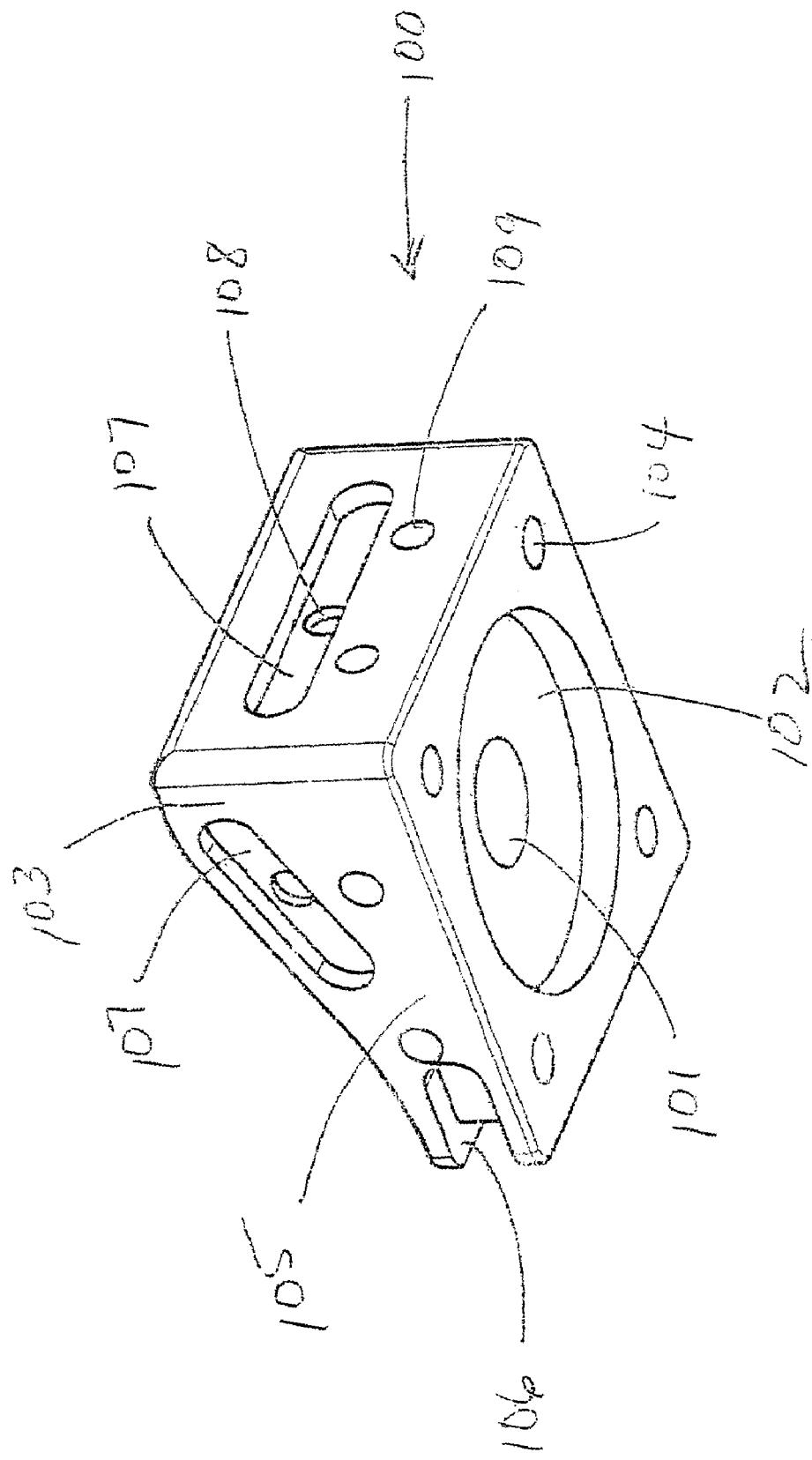
FIG. 18 is a further perspective taken from the bottom of the adapter bracket shown in FIG. 16.

FIGS. 16-18 illustrate another embodiment of an adapter bracket, denoted by the numeral 100. The adapter bracket 100 includes a centrally located bore 101, preferably tapped, extending from a top surface to a bottom surface of the adapter bracket 100. A circular recess 102 is provided about and co-axial with the bore 101 on the bottom surface of the adapter bracket 100, as shown in FIG. 18. As illustrated, the adapter bracket 100 has a generally square shape when viewed in plan from the top. Sidewalls 103 extend upwardly from the top surface on three of the sides, slanting downwardly to the top surface of the adapter bracket 100 on two of the opposed sidewalls 103. Threaded through-holes 104 are shown in each of the four corners within the sidewalls 103. The top and bottom surfaces of the adapter bracket 50 are generally flat other than the through-holes 104 and recess 102.

The sides 105 and sidewalls 103 of the adapter bracket 100 are provided with a plurality of undercut slots 106 and 107, respectively. Through-holes 108 are provided in the undercut slots 107. As illustrated, each through-hole 108 is located approximately centrally within the associated undercut slot 107. The sides 105 are provided with tapped holes 109 adapted to receive threaded fasteners. As illustrated, a pair of holes 109 is shown on each side.

An example of the use of the adapter bracket 50 follows. The specific details and dimensions are for illustration only.

Plaster Model Preparation

1) Took the cast over the cushioned liner or cast sock.
2) Filled the cast with plaster keeping the pipe 2" from the bottom of the cast.
3) Sealed the plaster model using an appropriate mold sealer such as cellulose crystals dissolved in acetone.
4) Tied a knot in the distal end of a non-stick nylon stockinette. Applied the non-stick nylon stockinette to the plaster model for a vacuum air wick. The knot should be centered on the distal end of the plaster model.
5) Painted the distal end of the cast around the knot in the nylon with a mold sealer such as cellulose crystals dissolved in acetone. This will glue down the nylon for trimming. Let dry and trimmed the nylon.
6) Attached the ⅜" four-hole fabrication spacer block to the adapter bracket 100 with the four 6 mm socket head cap screws. Tightened the four screws to the spacer block with a 6 mm hex key.
7) Installed the eight 5 mm hex socket set screws in the sides of the adapter bracket. The set screws protruded 3/16" for 3/16" plastic or ¼" for ¼" plastic to the mark the location for easy removal. Tightened with a 5 mm hex key.
8) Fastened the adapter bracket to the plaster model using double stick tape to secure the posterior foam to the adapter bracket and aligned or bench aligned the components. The Prosthetist should check and adjust the adapter bracket position for correct alignment. Nailed the foam to secure the adapter bracket to the model. Vacuum-formed the test socket using the blister or drape methods. For drape molding with an open non-welded seam, leave the plastic on one side of the Vivak. Place the side of the Vivak with the plastic facing up in the horizontal oven during the heat process. The oven temperature will vary 355-360 F for about 20 minutes. The side with the plastic on it will be turned toward the cast for vacuum forming and this will act as a separator. Fastener screws will be used to secure the plastic seam if this procedure is used.

Trimming

10) Let the thermoplastic socket cool down. Sanded off the plastic on top of the lock attachment bolt and remove the bolt with a hex key.
11) Trimmed out the ⅜" four-hole spacer block. Removed the four 6 mm socket head cap screws with a 6 mm hex key. Removed the four-hole spacer block.
12) Trimmed out and removed the thermoplastic socket from the plaster model. Sanded and buffed the trim lines.
13) Sanded off the plastic on top of the eight 5 mm hex socket set screws and remove screws with a 5 mm hex key.

Assembly

14) Installed and tightened the eight 5 mm socket head cap head screws and stainless steel washers to secure the attachment of the adapter bracket to the test socket. Tightened with a 5 mm hex key to a torque setting of 12 Nm or 9 foot pounds.
15) Installed the other endoskeletal components according to manufacturer's directions.

Filling the Thermoplastic Socket

16) Filled the locking pin hole with fitting gel or clay in order to prevent plaster from leaking into the lock mechanism. Taped over the foam contour on the inside of the socket with masking tape in order to prevent the plaster from leaking.

Figure 19:
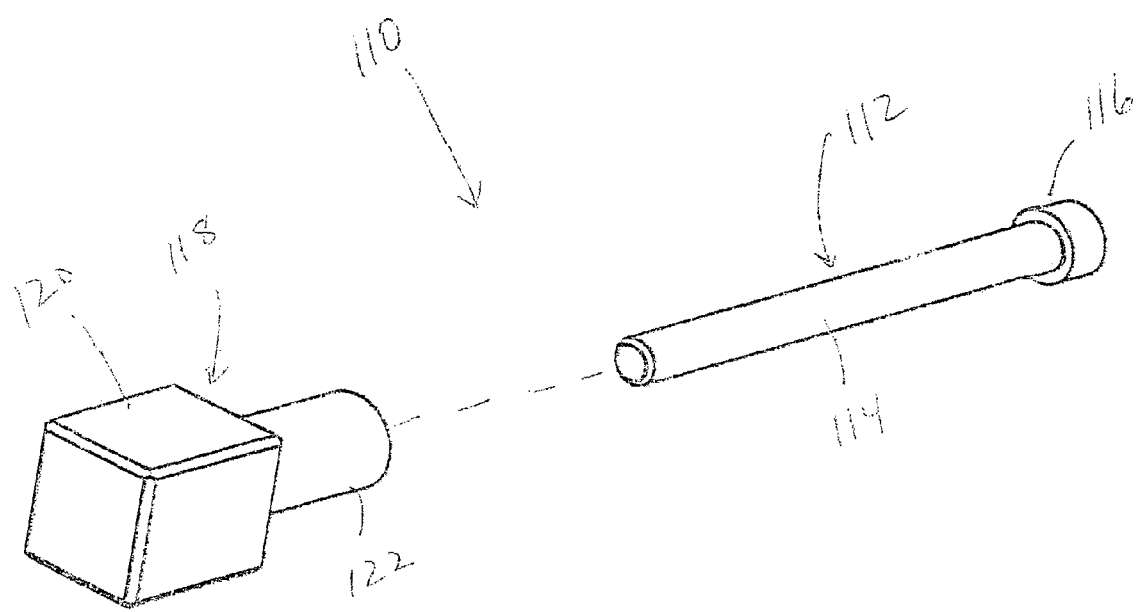
FIG. 19 is an exploded perspective view of an apparatus for forming a prosthetic device with transfer of proper alignment in accordance with the invention.

In a further aspect of the invention, a method is provided for transferring the alignment of a lock mechanism and/or socket attachment adapter bracket on a transtibial (below knee) or transfemoral (above knee) socket for a prosthesis with or without a suction locking liner with a locking pin and lock mechanism. In this regard, FIG. 19 shows an alignment retaining device, denoted generally by reference numeral 110. The alignment retaining device 110 includes an alignment screw 112 formed of a threaded shaft 114 that terminates in a head portion 116. The shaft 114 may be of different lengths to accommodate various lengths of lock mechanisms, pads and socket inserts.

Also provided is a head cap 118 having a body portion 120 and a threaded bore 122 adapted to threadedly engage the threaded shaft 116 of the screw 112. The cross-section of the body portion 120 of the head cap 118 is preferably formed with one or more corners and may be, for example, triangular, square, rectangular, pentagonal, hexagonal, etc. This configuration helps to prevent the head cap 118 from turning or coming out of the plaster during use.

An example of the use of the alignment retaining device 110 to form a test socket is as follows.

1. A suction locking liner is applied to the residual limb of the patient.

2. The lock pin is unscrewed from the liner and a hollow, internally threaded casting cylinder is attached to the end of the suction locking liner using an adapter have male threads on both ends.

3. A cast is made of the patient's residual limb and is reinforced around the casting cylinder with plaster bandage. The distal end of the casting cylinder is not covered with plaster bandage so that a wrench or screwdriver may subsequently be used to unscrew it from the suction locking liner.

4. After the cast has set, the casting cylinder is unscrewed and disengaged from the suction locking liner, and the adapter is removed from the end of the casting cylinder.

5. After the casting cylinder has been disengaged, the cast is removed from the patient's residual limb.

6. The alignment screw 112 is introduced into the end of the casting cylinder from the bottom, with the end of the threaded shaft 114 extending into the interior of the cast.

7. An O ring is applied over the shaft 114 of the alignment screw 112 in the interior of the cast and is pushed down until the O ring seals against the casting cylinder. Any void is filled with fitting gel or putty to prevent the plaster from leaking out when the cast is filled with plaster.

8. Reinforcing tape is applied over the bottom of the alignment screw 112 to ensure that the plaster does not leak.

9. The head cap or anchor 118 is then threaded onto the end of the alignment screw 112 until the head cap 118 is positioned about a ½ inch from the bottom of the cast.

10. A fill pipe is set to be in the cast about 1 inch from the top of the head cap 118.

11. The molding plaster is mixed with water and the cast is filled. The fill pipe is returned to the same position inside the cast and the plaster is allowed set.

12. The casting material is stripped off once the molding plaster has set, and the alignment screw 112 is unscrewed from the head cap 118 and removed.

13. The cast of the residual limb is then modified for proper weight bearing in the conventional manner.

Figure 20:
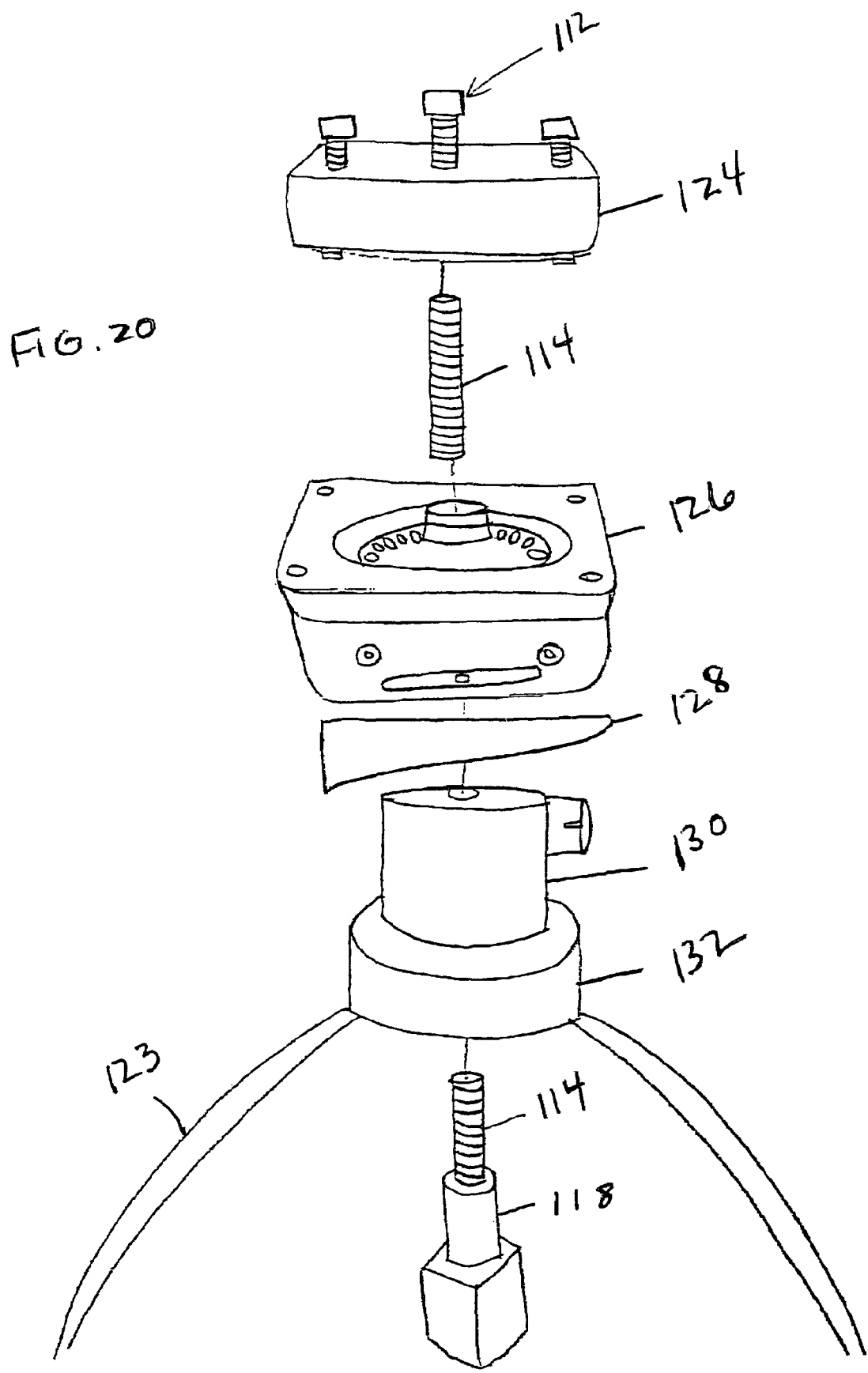
FIG. 20 is a somewhat schematic, exploded perspective view of the apparatus of FIG. 19 and prosthetic device.

Referring to FIG. 20, the alignment screw 112 is shown as introduced into the end of the plaster model 123 from the bottom, with the end of the threaded shaft 114 extending into the interior of the plaster model 123. The shaft 114 extends through the central aperture of a four-hole fabrication spacer block 124, which covers the bottom surface of an adapter bracket 126. A wedge member 128 may be positioned between the adapter bracket 126 and a lock 130. The wedge member 128 may be selected from an assortment of wedge members of varying degrees (such as 3, 5 or 7 degrees, as examples) to permit varying of the angle between the adapter bracket 126 and the lock 130 depending upon the needs of the patient. Alternative shapes to the wedge shown can be employed depending upon the structure of the lock utilized. An annular foam piece 132 is positioned on the end of the lock 130 opposite the adapter bracket 126. The head cap or anchor 118 is threaded onto the end of the alignment screw 112.

As another example of the invention, the alignment retaining device is used to fabricate a thermoplastic socket using an adapter bracket without a lock mechanism.

1. Nylon is applied to the plaster mold. The alignment screw 112 is threaded through a tapped hole in an adapter bracket with the center plug through hole. Examples of suitable adapter brackets are those shown in FIGS. 4-6 and 7-9.

2. The alignment screw 112 is screwed through the distal end of a foam piece and threaded onto the head cap or anchor 118 inside the plaster mold. The alignment screw 112 is tightened against the distal end foam until properly secured. The alignment of the adapter bracket is adjusted so that the hole pattern is properly oriented.

3. The thermoplastic socket is then fabricated in the conventional manner with the adapter bracket.

4. The alignment screw 112 is removed and the socket is trimmed out.

Figure 21:
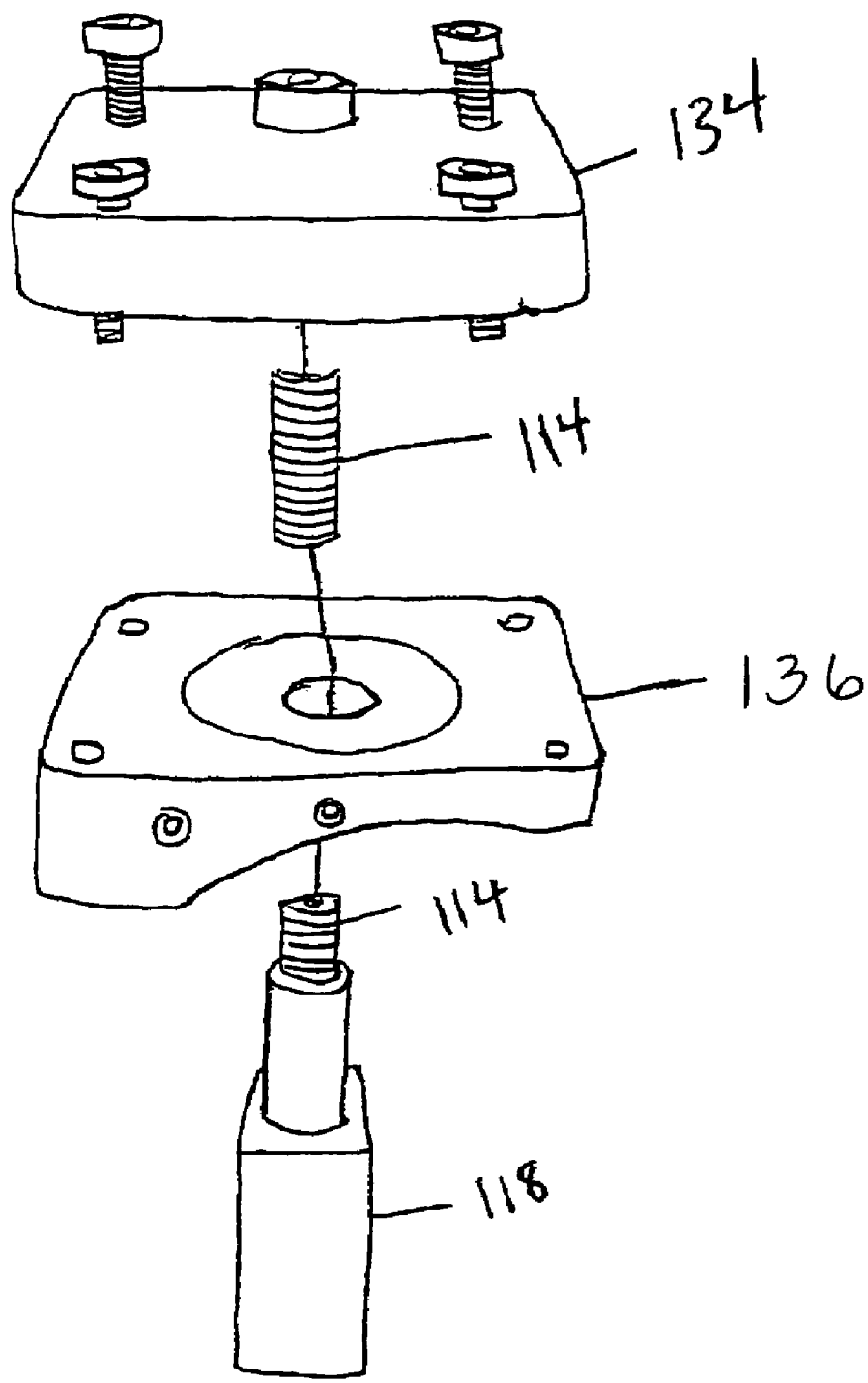
FIG. 21 is a somewhat schematic, exploded perspective view of the apparatus of FIG. 19 and prosthetic adapter bracket.

This is illustrated in FIG. 21, which shows the alignment screw 112 introduced through the hole in the distal end of the mold and threaded onto the head cap or anchor 118 inside the plaster mold. The shaft 114 extends through a four-hole fabrication spacer block 134, which covers the bottom surface of an adapter bracket 136. The alignment screw 112 is tightened against the fabrication spacer block 134 on the adapter bracket 136 until secured.

As a further example, the alignment retaining device is used to fabricate a thermoplastic socket using an adapter bracket and a lock mechanism.

1. Nylon is applied to the plaster mold. The adapter bracket with the center plug through-hole is installed and the alignment screw 112 is pushed through a fabrication block, the adapter bracket and a lock mechanism.

2. The alignment screw 112 is introduced through the hole in the distal end of the mold and threaded onto the head cap 118 inside the plaster mold. The alignment screw 112 is tightened against the fabrication block on the adapter bracket until secured.

3. The alignment of the adapter bracket and lock mechanism are adjusted as needed so that the attachment hole pattern is properly oriented.

4. The thermoplastic socket is then fabricated in the conventional manner with the adapter bracket and lock mechanism.

5. The alignment screw 112 is removed and the socket is trimmed out.

A still further example of the invention is the use of the alignment retaining device to fabricate a laminated socket using an adapter bracket without a lock mechanism.

1. Nylon is applied to the plaster mold and a PVA separator bag is installed. A piece of tape is applied over the hole for the bolt on the distal end of the plaster mold. A hole is punched in the tape and PVA bag for the bolt. The adapter bracket with the center plug through hole is installed by screwing the alignment screw 112 through the adapter bracket with threaded plug.

2. The alignment screw 112 is introduced through the hole in the distal end of the mold and threaded onto the head cap 118 inside the plaster mold. The alignment screw 112 is tightened until the adapter bracket is at the desired height above the mold, allowing sufficient room for the thickness of the lamination.

3. The lay-up is applied under the adapter bracket. The alignment of the adapter bracket is adjusted so that the attachment hole pattern is in the line of progression. The rest of the lay-up is applied over the adapter bracket. The PVA bag is applied and the socket is laminated.

4. The alignment screw 112 is removed and the socket is trimmed out.

Another example of the invention is the use of the alignment retaining device to fabricate a laminated socket using an adapter bracket and a lock mechanism.

1. Nylon is applied to the plaster mold and a PVA separator bag is installed. A piece of tape is applied over the hole for the bolt on the distal end of the plaster mold, and a hole punched in the tape and PVA bag for the bolt. The adapter bracket with the center plug through hole is attached. The alignment screw 112 is pushed through the fabrication block, adapter bracket and lock mechanism.

2. The alignment screw 112 is introduced through the hole in the distal end of the mold and screwed into the head cap 118 inside the plaster mold. The alignment screw 112 is tightened down against the fabrication block on the adapter bracket until properly secured. Enough room is allowed for the thickness of the lamination.

3. The lay-up is applied under the adapter bracket, and the alignment of the adapter bracket and lock mechanism is adjusted so that the hole pattern is in the line of progression. The rest of the lay-up is applied over the adapter bracket. The PVA bag is applied and the socket is laminated.

4. Then, the alignment screw 112 is removed and the socket is trimmed out.

The invention provides a method for transferring the alignment of a lock mechanism and/or socket attachment adapter bracket on a transtibial (below knee) or transfemoral (above knee) socket for a prosthesis with or without a suction locking liner with a locking pin and lock mechanism. The apparatus and method allow the transfer of socket alignment without the use of a vertical alignment transfer jig.

In accordance with the provisions of the patent statutes, the invention has been described in what is considered to represent its preferred embodiments. However, it should be noted that the invention can be practiced otherwise than as specifically illustrated and described without departing from its spirit or scope.

What is claimed is:

1. A method of forming a prosthetic residual limb socket based upon a test socket, comprising:

positioning an anchor within the test socket, the anchor being engaged with an alignment member extending out through a hole in the test socket;

introducing a molding material into the test socket so as to at least partially encase the anchor and allowing the molding material to set to form a model;

separating the test socket from the model and disengaging the anchor from the alignment member;

providing an adapter bracket having at least one through-hole adjacent the model and introducing the alignment member through the at least one through-hole in the adapter bracket and into engagement with the anchor to position the adapter bracket relative to the model;

forming a prosthetic residual limb socket about the model and adapter bracket;

disengaging the alignment member from the anchor; and separating the prosthetic residual limb socket from the model.

2. The method of claim 1, wherein the through-hole in the adapter bracket is tapped.

3. The method of claim 2, wherein the through-hole in the adapter bracket is a centrally located bore extending from a top surface to a bottom surface of the adapter bracket.

4. The method of claim 3, wherein the through-hole in the adapter bracket is adapted to receive one or more devices selected from the group consisting of a suction valve, air expulsion mechanism, pin cover, plug, and cosmetic adapter.

5. The method of claim 1, wherein the anchor comprises a shoulder portion to aid in preventing longitudinal movement of the anchor relative to the model.

6. The method of claim 1, wherein the anchor is provided with a cross sectional shape defined by at least one corner portion to aid in preventing rotational movement of the anchor relative to the model.

7. The method of claim 1, wherein the alignment member extends through the at least one through-hole in the adapter bracket and a foam block, and then into engagement with the anchor to position the adapter bracket relative to the model.

8. The method of claim 1, wherein a lock mechanism is secured to the adapter bracket and the alignment member extends through the lock mechanism into engagement with the anchor.

9. The method of claim 1, wherein the alignment member threadedly engages the anchor.

10. A method of forming a prosthetic residual limb test socket comprising:

providing an adapter bracket having an upper mounting face, a lower mounting face and a generally smooth sidewall extending therebetween, the sidewall including a plurality of bores in which a corresponding plurality of removable posts are received;

securing the adapter bracket to a model of a residual limb; and applying a socket forming material about at least a portion of the model and the adapter bracket, the socket forming material covering the plurality of removable posts but not the lower mounting face of the adapter bracket.

11. The method of claim 10, further comprising removing any socket forming material from the lower mounting face of the adapter bracket.

12. The method of claim 11, wherein any socket forming material is cut away from the lower mounting face of the adapter bracket.

13. The method of claim 10, wherein the socket forming material is applied in such a manner that the lower mounting face of the adapter bracket remains uncovered thereby.

14. The method of claim 10, wherein the plurality of removable posts comprise set-screws threadedly received in threaded bores in the adapter bracket.

15. The method of claim 10, further comprising removing that portion of the socket forming material which covers each of the plurality of posts, removing each of the plurality of posts from the respective bores in the adapter bracket, and moving the adapter bracket in the direction of the lower mounting face to separate the adapter bracket from the test socket.

16. The method of claim 10, wherein the socket forming material comprises a clear thermoplastic.

17. The method of claim 10, wherein a centrally located through-hole extends from a top surface to a bottom surface of the adapter bracket.

18. The method of claim 17, wherein the through-hole is tapped.

19. The method of claim 17, wherein the lower mounting face of the adapter bracket includes a circular recess about and coaxial with the centrally located through-hole.

* * * * *